(12) United States Patent
Nakamura

(10) Patent No.: US 10,500,311 B2
(45) Date of Patent: Dec. 10, 2019

(54) CELL STRUCTURE FOR BRAIN DAMAGE TREATMENT, PRODUCTION METHOD THEREOF, AND BRAIN DAMAGE TREATMENT AGENT

(71) Applicant: FUJIFILM Corporation, Tokyo (JP)

(72) Inventor: Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 148 days.

(21) Appl. No.: 15/380,350

(22) Filed: Dec. 15, 2016

(65) Prior Publication Data

US 2017/0095595 A1   Apr. 6, 2017

Related U.S. Application Data

(63) Continuation of application No. PCT/JP2015/067133, filed on Jun. 15, 2015.

(30) Foreign Application Priority Data

Jun. 16, 2014 (JP) .................................. 2014-123226

(51) Int. Cl.

| | |
|---|---|
| A61L 27/38 | (2006.01) |
| A61L 27/14 | (2006.01) |
| A61L 27/56 | (2006.01) |
| A61L 27/00 | (2006.01) |
| A61K 35/28 | (2015.01) |
| C07K 14/78 | (2006.01) |
| A61L 27/22 | (2006.01) |

(52) U.S. Cl.
CPC .......... *A61L 27/3878* (2013.01); *A61K 35/28* (2013.01); *A61L 27/00* (2013.01); *A61L 27/222* (2013.01); *A61L 27/3808* (2013.01); *A61L 27/3834* (2013.01); *A61L 27/56* (2013.01); *C07K 14/78* (2013.01); *A61L 2430/32* (2013.01)

(58) Field of Classification Search
None
See application file for complete search history.

(56) References Cited

U.S. PATENT DOCUMENTS

| | | | |
|---|---|---|---|
| 9,211,266 B2 | 12/2015 | Iwazawa et al. | |
| 2006/0210550 A1 | 9/2006 | Inoue et al. | |
| 2010/0322908 A1 | 12/2010 | Everland et al. | |
| 2012/0263681 A1 | 10/2012 | Miyoshi et al. | |
| 2012/0329157 A1 | 12/2012 | Nakamura | |
| 2013/0071441 A1 | 3/2013 | Iwazawa et al. | |
| 2015/0202344 A1 | 7/2015 | Iwazawa et al. | |
| 2015/0272998 A1 | 10/2015 | Miyoshi et al. | |

FOREIGN PATENT DOCUMENTS

| | | |
|---|---|---|
| JP | 2004-143067 A | 5/2004 |
| JP | 2005-035945 A | 2/2005 |
| JP | 2011-512810 A | 4/2011 |
| JP | 2012-82245 A | 4/2012 |
| JP | 2012-219100 A | 11/2012 |
| JP | 2014-012114 A | 1/2014 |
| WO | 2011/108517 A1 | 9/2011 |
| WO | 2014/133081 A1 | 9/2014 |
| WO | 2015/046216 A1 | 4/2015 |

OTHER PUBLICATIONS

Office Action dated Nov. 7, 2017, issued by the Japanese Patent Office in counterpart Japanese Application No. 2016-529322.
International Search Report of PCT/JP2015/067133, dated Aug. 18, 2015. [PCT/ISA/210].
Written Opinion of PCT/JP2015/067133, dated Aug. 18, 2015. [PCT/ISA/237].
Guan Jian et al., "Transplantation of human mesenchymal stem cells loaded on collagen scaffolds for the treatment of traumatic brain injury in rats," Biomaterials, 2013, vol. 34, No. 24, p. 5937-5946.
Satoshi Kuroda et al., "IV. Chriyoho 3. Kotsuzui Kanshitsu Saibo Ishoku ni yoru Chusu Shinkei Saisei—Saikin no Shinpo," Annual Review Shinkei 2007, 2007, pp. 85-95, p. 85, right column, lines 15 to 21.
International Preliminary Report on Patentability dated Dec. 29, 2016 from the International Bureau in counterpart International Application No. PCT/JP2015/067133.
Extended European Search Report dated Jul. 19, 2017, issued by the European Patent Office in counterpart European Application No. 15809738.6.
Communication dated Oct. 17, 2019 issued in European Application No. 15 809 738.6.

*Primary Examiner* — Michelle F. Paguio Frising
(74) *Attorney, Agent, or Firm* — Sughrue Mion, PLLC

(57) ABSTRACT

An object of the present invention is to provide a cell structure for brain damage treatment which does not contain glutaraldehyde and in which it is possible to exhibit a sufficient effect of treating brain damage, a production method thereof, and a brain damage treatment agent. According to the present invention, there is provided a cell structure for brain damage treatment which contains biocompatible macromolecular blocks and at least one kind of cell and in which a plurality of the biocompatible macromolecular blocks are disposed in gaps between a plurality of the cells, in which the tap density of the biocompatible macromolecular block is 10 mg/cm$^3$ to 500 mg/cm$^3$ or a value obtained by dividing a square root of a cross-sectional area in a two-dimensional cross-sectional image of the biocompatible macromolecular block by a peripheral length is 0.01 to 0.13.

33 Claims, 13 Drawing Sheets
Specification includes a Sequence Listing.

ANGIOGENESIS IN hMSC MOSAIC CELL AGGREGATION
2 WEEKS AFTER TRANSPLANTATION

BLOOD VESSELS ARE FORMED
63 PIECES/mm$^2$

ANGIOGENESIS IN hMSC + hECFC MOSAIC CELL AGGREGATION
2 WEEKS AFTER TRANSPLANTATION

THERE ARE MANY BLOOD
VESSELS FORMED
180 PIECES/mm$^2$

FIG. 6A
SPACE OCCUPANCY RATE OF EACH HOLLOW HOLE SIZE IN POROUS BODY
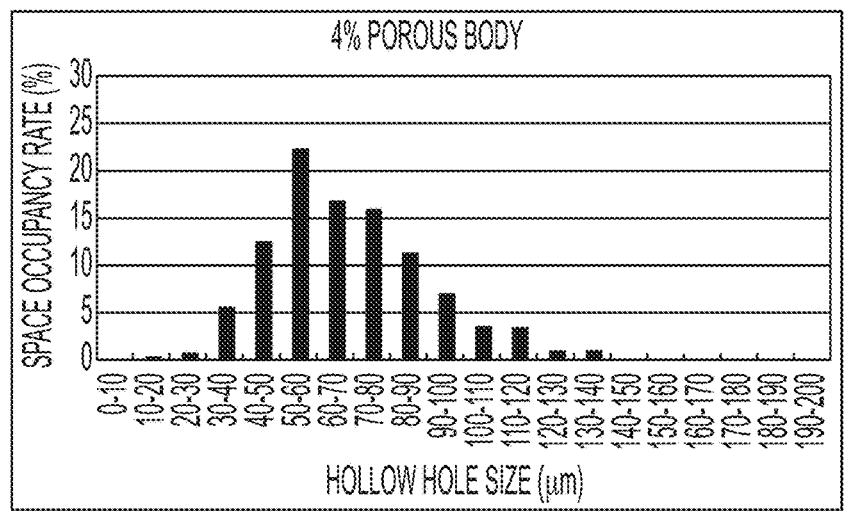
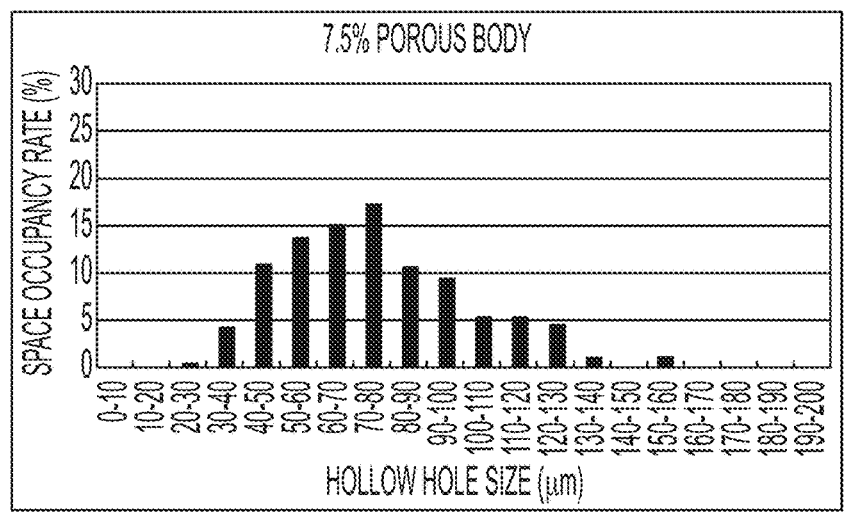
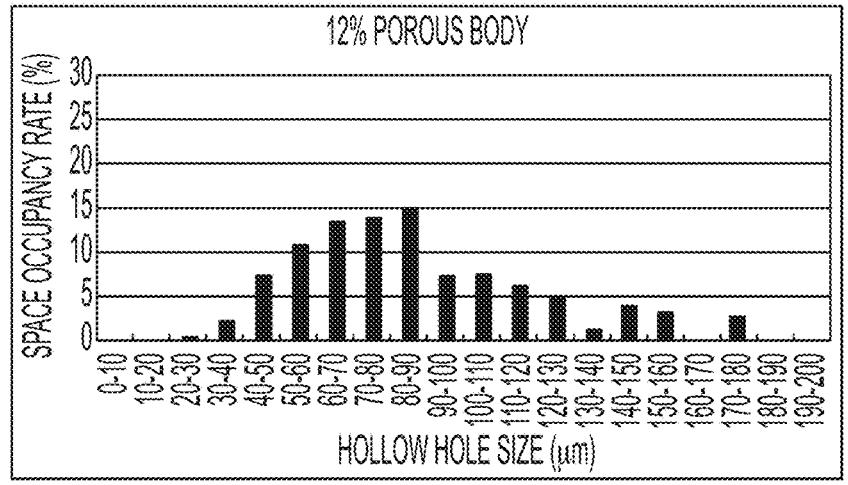

FIG. 6B
SPACE OCCUPANCY RATE OF EACH HOLLOW HOLE SIZE IN POROUS BODY
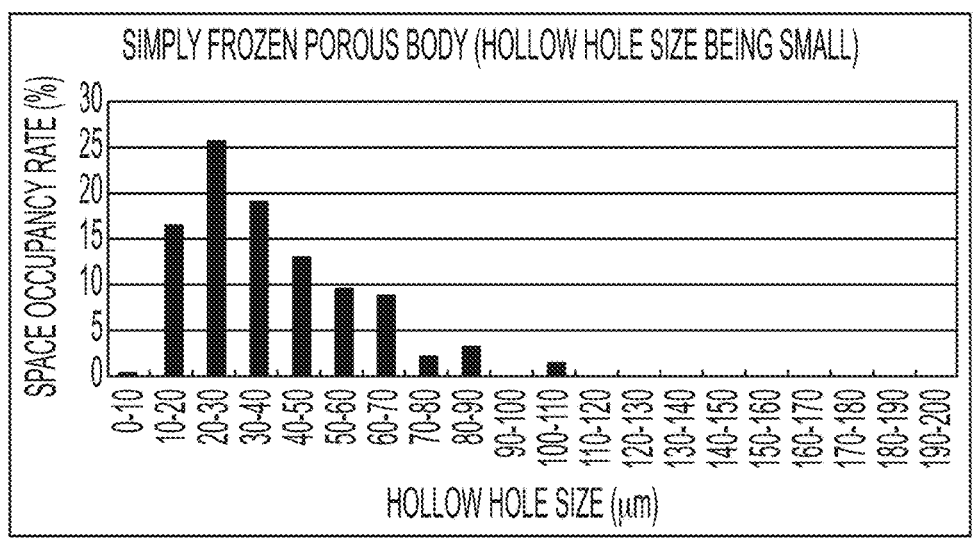
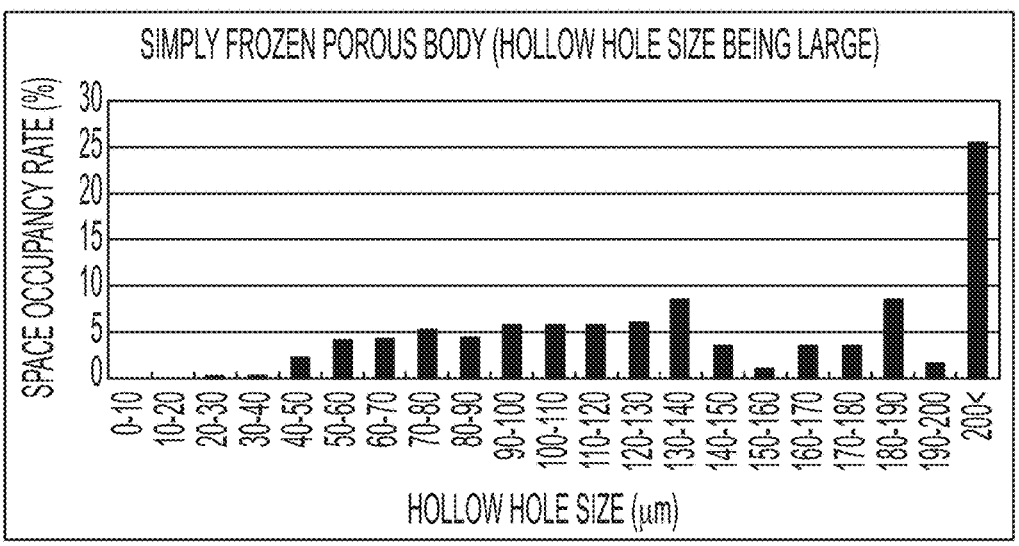

FIG. 9
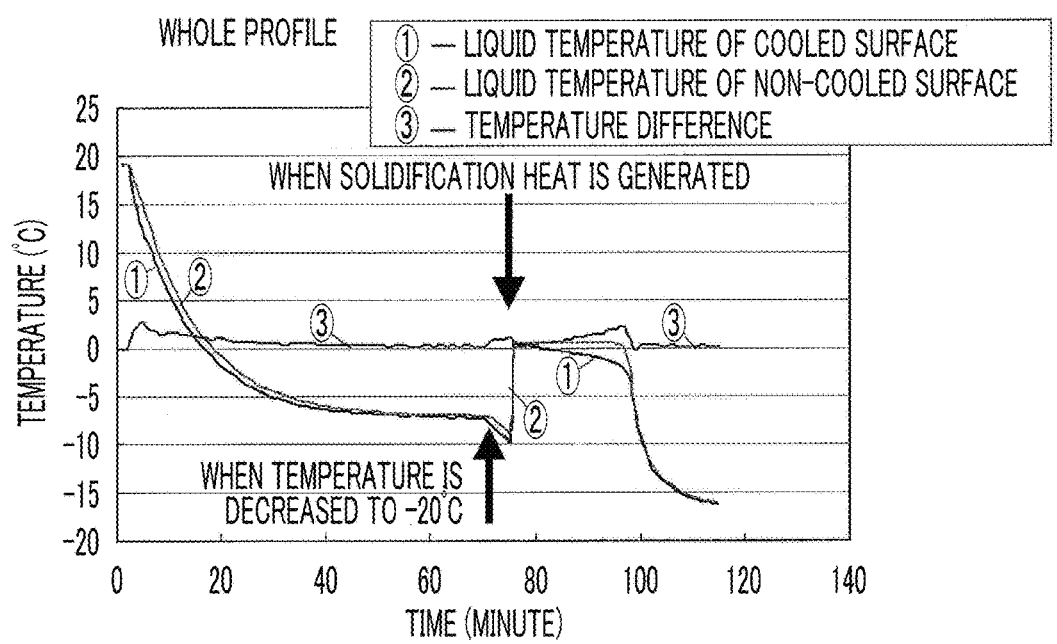
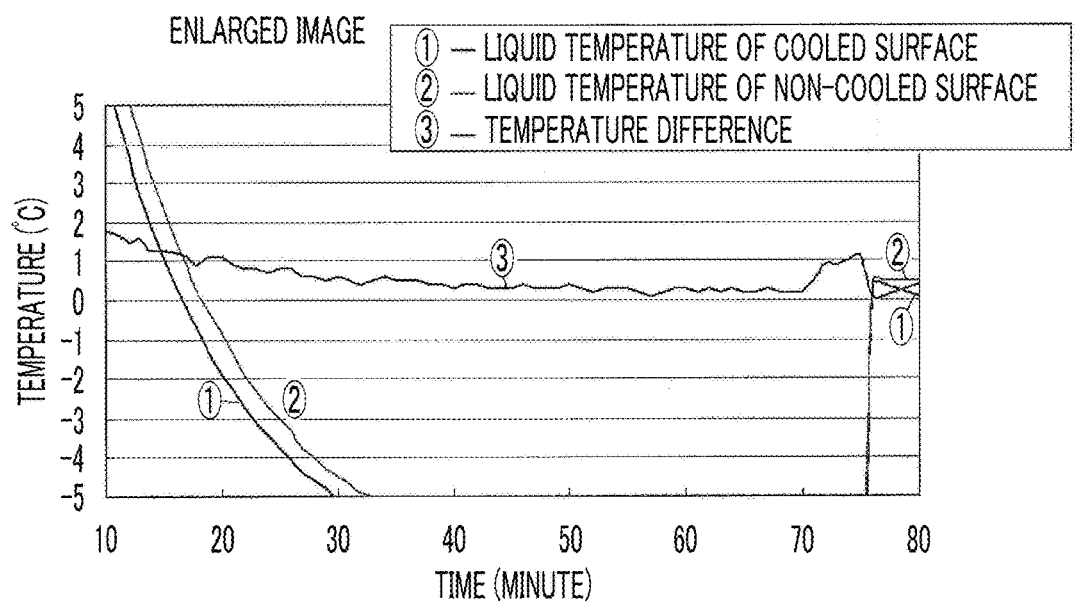

SEQUENCE LISTING

<160> NUMBER OF SEQ ID NOS: 10

<210> SEQ ID NO 1
<211> LENGTH: 571
<212> TYPE: PRT
<213> ORGANISM: Artificial Sequence
<220> FEATURE:
<223> OTHER INFORMATION: Synthetic recombinant peptide sequence

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

```
Pro Lys Gly Glu Arg Gly Asp Ala Gly Pro Lys Gly Asp Gly Ala
            355                 360                 365
Pro Gly Lys Asp Gly Val Arg Gly Leu Ala Gly Pro Gly Ala Pro
    370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
                420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
    450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
    515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      adhesive sequence
```

-continued

```
<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 9

Asp Gly Glu Ala
1
```

```
<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 10

Glu Arg Gly Asp
1
```

CELL STRUCTURE FOR BRAIN DAMAGE TREATMENT, PRODUCTION METHOD THEREOF, AND BRAIN DAMAGE TREATMENT AGENT

CROSS-REFERENCE TO RELATED APPLICATIONS

The present application is a continuation of PCT/JP2015/067133 filed on Jun. 15, 2015 and claims priority under 35 U.S.C. § 119 of Japanese Patent Application No. 123226/2014 filed on Jun. 16, 2014.

BACKGROUND OF THE INVENTION

1. Field of the Invention

The present invention relates to a cell structure for brain damage treatment, a production method thereof, and a brain damage treatment agent. The present invention particularly relates to a cell structure for brain damage treatment in which biocompatible macromolecular blocks are disposed in gaps between cells, a production method thereof, and a brain damage treatment agent.

2. Description of the Related Art

Currently, regenerative medicine, which regenerates living body tissues and organs having functional disorders or dysfunction, is put into practical use. The regenerative medicine is new medical technology creating a form or a function of a living body tissue that cannot be recovered with only natural healing ability possessed by a living body, which is the same as that of an original tissue, again, using three factors including a cell, a scaffold, and a growth factor. In recent years, treatment using cells is gradually realized. Examples thereof include cartilage treatment using autologous chondrocytes, and cultured epidermis using autologous cells; bone regeneration treatment using mesenchymal stem cells; myocardial cell sheet treatment using myoblasts; cornea regeneration treatment using corneal epithelial sheets; and nerve regeneration treatment. These kinds of new treatment are different from alternative medicine (for example, a bone prosthetic material or hyaluronic acid injection) using an artifact in the related art, and repair and regenerate biological tissues, thereby obtaining a high treatment effect. Actually, products such as cultured epidermis or cultured cartilage using autologous cells have been available on the market.

A cell structure, which contains cells and macromolecular blocks having biocompatibility, and in which the plurality of the above-described macromolecular block are arranged in gaps between the plurality of the above-described cells, is disclosed in WO2011/108517A. In the cell structure disclosed in WO2011/108517A, it is possible to deliver nutrients to the inside of the cell structure from the outside. The cell structure has a sufficient thickness, and cells exist in the structure uniformly. In Example of WO2011/108517A, high cell survival activity is verified using a macromolecular block formed of a recombinant gelatin material or a natural gelatin material. A cell structure for cell transplantation, which contains a macromolecular block having biocompatibility and at least one kind of cell, and in which the plurality of the above-described macromolecular blocks are arranged in the gaps between the plurality of the above-described cells, is disclosed in JP2014-12114A. In Example of JP2014-12114A, angiogenesis is evaluated using the cell structure for cell transplantation.

In addition, it has also been reported that a disease is treated through cell transplantation. For example, a composition including a physiologically active substance and cells is disclosed in JP2005-35945A and the fact that a combination therapy using a hepatocyte growth factor (HGF) and vascular endothelial cells is effective for regenerating brain tissue is disclosed in JP2005-35945A. In addition, a neovascularization-inducing agent containing fibrin, an in-vivo degradable polymer, and cells is disclosed in JP2004-143067A. Furthermore, it is disclosed in JP2012-219100A that central nervous system disorder such as cerebral stroke is treated using a cell-containing composition in which bone marrow stromal cells, into which a Notch gene and/or a Notch signal transmission-related gene are/is introduced, are adhered to biocompatible polymers.

SUMMARY OF THE INVENTION

In the macromolecular block of the cell structure disclosed in Examples of WO2011/108517A and JP2014-12114A, glutaraldehyde is used for cross-linking of macromolecules. In order for cell transplantation treatment performed on a human body, it is desirable to use a cell structure which is produced through a method in which glutaraldehyde is not used. However, efficacy of a cell structure, which has been produced through the method in which glutaraldehyde is not used, with respect to brain damage treatment has not yet been reported.

Although the combination therapy of administering HGF and vascular endothelial cells to brain tissue is disclosed in JP2005-35945A, improvement of a motor function after cerebral infarction is not evaluated. Therefore, it is unclear whether or not a sufficient effect of treating brain damage is exhibited. In the neovascularization-inducing agent disclosed in JP2004-143067A, it is necessary to use fibrin, improvement of a motor function after cerebral infarction has not been evaluated, and it is unclear whether or not a sufficient effect of treating brain damage is exhibited. In addition, in the composition disclosed in JP2012-219100A, cells, which have specific properties, such as cells obtained by introducing a Notch gene and/or a Notch signal transmission-related gene into bone marrow stromal cells, or cells obtained by culturing bone marrow stromal cells under a special condition, are used.

An object of the present invention is to provide a cell structure for brain damage treatment which does not contain glutaraldehyde and in which necrosis of transplanted cells is suppressed (that is, it is excellent in cell viability) and it is possible to exhibit a sufficient effect of treating brain damage, a production method thereof, and a brain damage treatment agent.

The present inventors have conducted extensive studies in order to solve the above-described problems. As a result, they have found that, when producing a cell structure for cell transplantation by disposing a plurality of biocompatible macromolecular blocks in gaps between a plurality of cells using the biocompatible macromolecular blocks and at least one kind of cell, it is possible to provide a cell structure in which necrosis of transplanted cells is suppressed (that is, these are excellent in cell viability) using biocompatible macromolecular blocks of which the tap density is 10 mg/cm$^3$ to 500 mg/cm$^3$ or a value obtained by dividing a square root of a cross-sectional area in a two-dimensional cross-sectional image by a peripheral length is 0.01 to 0.13. Furthermore, the present inventors have found that it is possible to improve a motor function of a rat by administering the above-described cell structure to a rat with cerebral infarction. The present invention has been completed based on these findings.

That is, according to the present invention, the following inventions are provided.

(1) A cell structure for brain damage treatment which contains biocompatible macromolecular blocks and at least one kind of cell and in which a plurality of the above-described biocompatible macromolecular blocks are disposed in gaps between a plurality of the above-described cells, in which the tap density of the above-described biocompatible macromolecular block is 10 mg/cm$^3$ to 500 mg/cm$^3$ or a value obtained by dividing a square root of a cross-sectional area in a two-dimensional cross-sectional image of the above-described biocompatible macromolecular block by a peripheral length is 0.01 to 0.13.

(2) The cell structure for brain damage treatment according to (1), in which the above-described cells include at least mesenchymal stem cells and/or bone marrow cells.

(3) The cell structure for brain damage treatment according to (1) or (2), in which the number of cells, to be administered, per administration is $1.0 \times 10^5$ to $1.0 \times 10^7$ pieces/kg body weight.

(4) The cell structure for brain damage treatment according to any one of (1) to (3), in which the brain damage includes brain injury, hypoxic-ischemic brain damage, cerebral infarction, and/or cerebral stroke.

(5) The cell structure for brain damage treatment according to any one of (1) to (4), in which the size of one of the above-described biocompatible macromolecular blocks is 10 μm to 300 μm.

(6) The cell structure for brain damage treatment according to any one of (1) to (5), in which the thickness or the diameter of the above-described cell structure is 400 μm to 3 cm.

(7) The cell structure for brain damage treatment according to any one of (1) to (6), in which the above-described cell structure includes 0.0000001 μg to 1 μg of a biocompatible macromolecular block per cell.

(8) The cell structure for brain damage treatment according to any one of (1) to (7), in which the above-described biocompatible macromolecular block consists of a recombinant peptide.

(9) The cell structure for brain damage treatment according to (8), in which the above-described recombinant peptide is any of a peptide formed of an amino acid sequence described in SEQ ID No: 1, a peptide formed of an amino acid sequence in which one or a plurality of amino acids are deleted, substituted, or added in the amino acid sequence described in SEQ ID No: 1, and has biocompatibility, or a peptide formed of an amino acid sequence having 80% or more sequence identity to the amino acid sequence described in SEQ ID No: 1, and has biocompatibility.

(10) The cell structure for brain damage treatment according to any one of (1) to (9), in which, in the above-described biocompatible macromolecular block, the above-described biocompatible macromolecules are cross-linked using heat, ultraviolet rays, or enzymes.

(11) The cell structure for brain damage treatment according to any one of (1) to (10), in which the above-described biocompatible macromolecular block is in a granule form obtained by grinding a porous body of a biocompatible macromolecule.

(12) The cell structure for brain damage treatment according to any one of (1) to (11), in which the above-described biocompatible macromolecular block is a biocompatible macromolecular block produced through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and a step (b) of freeze-drying the frozen biocompatible macromolecules which have been obtained in the above-described step (a).

(13) The cell structure for brain damage treatment according to any one of (1) to (12), in which the above-described biocompatible macromolecular block is a biocompatible macromolecular block produced through a method including the step (a) of freezing the solution of the biocompatible macromolecules through the freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, the step (b) of freeze-drying the frozen biocompatible macromolecules which have been obtained in the above-described step (a), and a step (c) of grinding a porous body which has been obtained in the above-described step (b).

(14) The cell structure for brain damage treatment according to (12) or (13), in which, in the above-described step (a), the highest internal liquid temperature, which is a liquid temperature in a portion having the highest liquid temperature within the solution becomes lower than or equal to a temperature which is 7° C. lower than a melting point of a solvent in an unfrozen state.

(15) The cell structure for brain damage treatment according to any one of (1) to (14), in which the above-described cell structure is a cell structure obtained by mixing the above-described biocompatible macromolecular blocks and the above-described cells and culturing the mixture for 10 hours or longer.

(16) A cell structure for brain damage treatment which is obtained by merging a plurality of the cell structures for brain damage treatment according to any one of (1) to (15).

(17) A method for producing the cell structure for brain damage treatment according to any one of (1) to (16), the method comprising: a step of mixing cells and biocompatible macromolecular blocks of which the tap density is 10 mg/cm$^3$ to 500 mg/cm$^3$ or a value obtained by dividing a square root of a cross-sectional area in a two-dimensional cross-sectional image by a peripheral length is 0.01 to 0.13, and culturing the mixture for 10 hours or longer.

(18) A brain damage treatment agent comprising: the cell structure for brain damage treatment according to any one of (1) to (16).

(19) A method for treating brain damage, the method comprising: a step of administering the cell structure for brain damage treatment according to any one of (1) to (16) to a patient with brain damage.

(20) Use of the cell structure for brain damage treatment according to any one of (1) to (16) for producing a brain damage treatment agent.

The cell structure for brain damage treatment and the brain damage treatment agent of the present invention are safe for a human body since these can be produced without using glutaraldehyde. The cell structure for brain damage treatment and the brain damage treatment agent of the present invention suppress necrosis of transplanted cells (that is, these are excellent in cell viability), and therefore, it is possible to effectively treat brain damage such as cerebral infarction.

BRIEF DESCRIPTION OF THE DRAWINGS

FIG. 6A and FIG. 613 shows a space occupancy rate of each hollow hole size in porous bodies.

FIG. 9 shows a liquid temperature profile while producing a CBE3 porous body.

DESCRIPTION OF THE PREFERRED EMBODIMENTS

Figure 1:
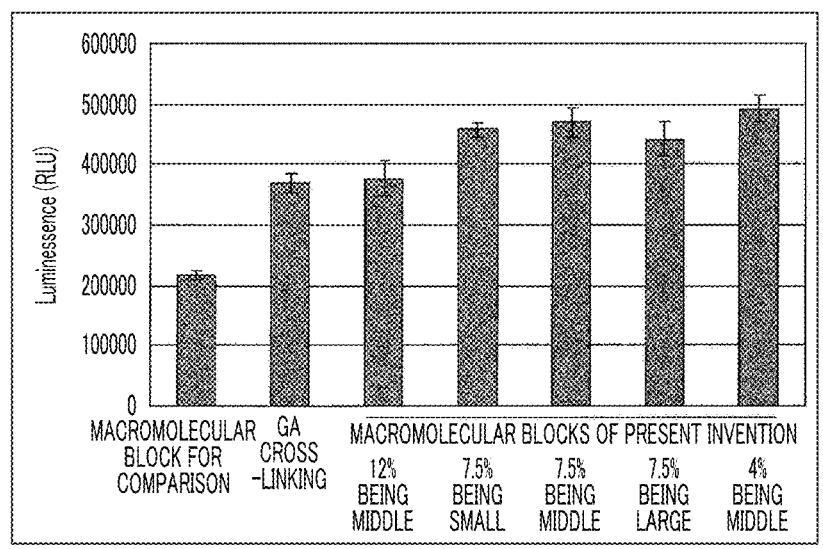
FIG. 1 shows a difference in an in vitro ATP assay depending on blocks.

Hereinafter, an embodiment of the present invention will be described in detail.

The present invention relates to a cell structure for brain damage treatment which contains biocompatible macromolecular blocks and at least one kind of cell and in which a plurality of the biocompatible macromolecular blocks are disposed in gaps between a plurality of the cells, in which the tap density of the biocompatible macromolecular block is 10 mg/cm$^3$ to 500 mg/cm$^3$ or a value obtained by dividing a square root of a cross-sectional area in a two-dimensional cross-sectional image of the biocompatible macromolecular block by a peripheral length is 0.01 to 0.13; a production method thereof; and a brain damage treatment agent containing the above-described cell structure for brain damage treatment. In the present specification, in some cases, the cell structure of the present invention is also referred to as a mosaic cell aggregation (a cell aggregation in a mosaic shape).

(1) Biocompatible Macromolecular Blocks (1-1) Biocompatible Macromolecules

Biocompatibility means a property which does not cause a significantly harmful reaction such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable materials include polypeptide (for example, gelatin or the like to be described below) such as recombinant peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, recombinant peptide is particularly preferable. Devising of an improvement of cell adhesion properties in these biocompatible macromolecules may be performed. Specifically, methods such as "coating of the surface of a base material with a cell adhesion substrate (fibronectin, vitronectin, or laminin) or peptides of a cell adhesion sequence (an RGD sequence, an LDV sequence, an REDV sequence (SEQ ID No: 2), a YIGSR sequence (SEQ ID No: 3), a PDSGR sequence (SEQ ID No: 4), an RYVVLPR sequence (SEQ ID No: 5), an LGTIPG sequence (SEQ ID No: 6), an RNIAEIIKDI sequence (SEQ ID No: 7), an IKVAV sequence (SEQ ID No: 8), an LRE sequence, a DGEA sequence (SEQ ID No: 9), and a HAV sequence, which are represented by one-letter notation of amino acids)", "aminization or cationization of the surface of a base material", or "plasma treatment performed on the surface of a base material or hydrophilic treatment due to corona discharge" can be used.

The kinds of polypeptides containing recombinant peptides are not particularly limited as long as polypeptides have biocompatibility. For example, gelatin, collagen, elastin, fibronectin, ProNectin, laminin, tenascin, fibrin, fibroin, entactin, thrombospondin, and RetroNectin are preferable and gelatin, collagen, and atelocollagen are most preferable. As the gelatin to be used in the present invention, natural gelatin or recombinant gelatin is preferable and recombinant gelatin is more preferable. The natural gelatin referred to herein means gelatin produced using naturally derived collagen. The recombinant gelatin will be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163-173 (1954), "Area of Chemistry" vol. 11, 10, pp. 719-725 (1957), and "Fragrance Journal, vol. 50, pp. 79-82 (1981). Briefly, the root of every organic compound is set to methane ($CH_4$), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram—Foundation and Application-" (written by Yoshio KOUDA, Sankyo Shuppan Co., Ltd., 2008). In the present specification, the hydrophilic and hydrophobic properties are represented by a "1/IOB" value which was obtained by taking a reciprocal number of JOB. This is a notation of representing more hydrophilic properties as the "1/IOB" value becomes small (close to 0).

The hydrophilic properties and water absorbency become high by making the "1/IOB" value of the biocompatible macromolecules used in the present invention be within the above-described range, which effectively acts to hold nutrient components. As a result, it is estimated that this point contributes to stability of cells and easy survival of cells in a cell structure (mosaic cell aggregation).

In a case where the biocompatible macromolecules used in the present invention are polypeptides, the hydrophilic and hydrophobic indexes represented by a grand average of hydropathicity (GRAVY) value is preferably −9.0 to 0.3, and more preferably −7.0 to 0.0. The grand average of hydropathicity (GRAVY) value can be obtained through "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appeal R. D., Bairoch A.; ExPASy: the proteomics server for in-depth protein knowledge and analysis.; Nucleic Acids Res. 31:3784-3788 (2003)".

The hydrophilic properties and water absorbency become high by making the GRAVY value of the biocompatible macromolecules used in the present invention be within the above-described range, which effectively acts to hold nutrient components. As a result, it is estimated that this point contributes to stability of cells and easy survival of cells in a cell structure (mosaic cell aggregation).

(1-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As a general cross-linking method, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known. In the present invention, it is preferable to use a cross-linking method in which glutaraldehyde is not used. In the present invention, it is more preferable to use a cross-linking method in which aldehydes or condensation agents are not used. That is, the biocompatible macromolecular blocks in the present invention are preferably biocompatible macromolecular blocks which do not contain glutaraldehyde, and are more preferably biocompatible macromolecular blocks which do not contain aldehydes or condensation agents. As the cross-linking method used in the present invention, thermal cross-linking, ultraviolet cross-linking, or enzymatic cross-linking is more preferable, and thermal cross-link is particularly preferable.

In a case of performing cross-linking using an enzyme, there is no particular limitation as long as the enzyme has a cross-linking action between macromolecular materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa: Haematologic Technologies, Inc).

The reaction temperature when performing cross-linking (for example, thermal cross-linking) is not particularly limited as long as cross-linking can be performed, but is preferably −100° C. to 500° C., more preferably 0° C. to 300° C., still more preferably 50° C. to 300° C., still more preferably 100° C. to 250° C., and still more preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, and to use recombinant gelatin disclosed in, for example, EP1014176A2, U.S. Pat. No. 6,992,172B, WO2004/85473A, and WO2008/103041A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2 kDa to 100 kDa, more preferably 2.5 kDa to 95 kDa, still more preferably 5 kDa to 90 kDa, and most preferably 10 kDa to 90 kDa.

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV sequence (SEQ ID No: 2), a YIGSR sequence (SEQ ID No: 3), a PDSGR sequence (SEQ ID No: 4), an RYVVLPR sequence (SEQ ID No: 5), an LGTIPG sequence (SEQ ID No: 6), an RNIAEIIKDI sequence (SEQ ID No: 7), an IKVAV sequence (SEQ ID No: 8), an LRE sequence, a DGEA sequence (SEQ ID No: 9), and a HAV sequence, which are represented by one-letter notation of amino acids are preferable in that there are many kinds of cells adhered. An RGD sequence, a YIGSR sequence (SEQ ID No: 3), a PDSGR sequence (SEQ ID No: 4), an LGTIPG sequence (SEQ ID No: 6), an IKVAV sequence (SEQ ID No: 8), and a HAV sequence are more preferable and an RGD sequence is particularly preferable. In the RGD sequence, an ERGD sequence (SEQ ID No: 10) is preferable. It is possible to improve the production amount of substrate of a cell using recombinant gelatin having cell adhesion signals. For example, it is possible to improve the production of glycosaminoglycan (GAG) in a case of cartilage differentiation using mesenchymal stem cells as cells.

As arrangement of RGD sequences in recombinant gelatin used in the present invention, it is preferable that the number of amino acids between RGDs is between 0 to 100 and preferably between 25 to 60 without being even.

The content of this minimum amino acid sequence is preferably 3 to 50, more preferably 4 to 30, and particularly preferably 5 to 20 in one molecule of protein in view of cell adhesion properties and proliferation properties. The most preferable content thereof is 12.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is still more preferably at least 0.6%, still more preferably at least 0.8%, still more preferably at least 1.0%, still more preferably at least 1.2%, and most preferably at least 1.5%. The number of RGD motifs within a recombinant peptides is, per 250 amino acids, preferably at least 4, still more preferably 6, still more preferably 8, and still more preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin used in the present invention contains at least two RGD sequences per 250 amino acids, more preferably contains at least three RGD sequences per 250 amino acids, and still more preferably contains at least four RGD sequences per 250 amino acids. As a further mode of the recombinant gelatin used in the present invention, the recombinant gelatin contains at least four RGD motifs, preferably 6 RGD motifs, more preferably 8 RGD motifs, and still more preferably 12 to 16 RGD motifs.

In addition, the recombinant gelatin may be partially hydrolyzed.

The recombinant gelatin used in the present invention is preferably represented by Formula: A-[(Gly-X-Y)$_m$]$_m$-B. n pieces of X each independently represent any amino acid and n pieces of Y each independently represent any amino acid. m is preferably 2 to 10 and more preferably 3 to 5. n is preferably 3 to 100, more preferably 15 to 70, and most preferably 50 to 65. A represents an arbitrary amino acid or an amino acid sequence, B represents an arbitrary amino acid or an amino acid sequence, n pieces of X each independently represent any amino acid, and n pieces of Y each independently represent any amino acid.

More preferably, the recombinant gelatin used in the present invention is represented by Formula: Gly-Ala-Pro-[(Gly-X-Y)63]3-Gly (where 63 pieces of X each independently represent any amino acid and 63 pieces of Y each independently represent any amino acid. 63 pieces of Gly-X-Y may be the same as or different from each other).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and still more preferably 7 to 9.5.

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of (1) a peptide formed of an amino acid sequence described in SEQ ID No: 1;

(2) a peptide formed of an amino acid sequence in which one or a plurality of amino acids are deleted, substituted, or added in the amino acid sequence described in SEQ ID No: 1, and has biocompatibility; or (3) a peptide formed of an amino acid sequence having 80% or more (more preferably 90% or more, particularly preferably 95% or more, and most preferably 98% or more) sequence identity to the amino acid sequence described in SEQ ID No: 1, and has biocompatibility.

"One or a plurality of" in the "amino acid sequence in which one or a plurality of amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Macromolecular Block

In the present invention, a block (aggregation) consisting of the above-described biocompatible macromolecules is used.

The shape of the biocompatible macromolecular block in the present invention is not particularly limited. Examples thereof include an amorphous shape, a spherical shape, a particulate shape, a powdery shape, a porous shape, a fibrous shape, a spindle shape, a flat shape, and a sheet shape. An amorphous shape, a spherical shape, a particulate shape, a powdery shape, and a porous shape are preferable and an amorphous shape is more preferable. The amorphous shape indicates that the shape of a surface is uneven, and indicates, for example, an object, such as rock, which has roughness.

The tap density of the biocompatible macromolecular block in the present invention is 10 mg/cm$^3$ to 500 mg/cm$^3$, preferably 20 mg/cm$^3$ to 400 mg/cm$^3$, more preferably 40 mg/cm$^3$ to 220 mg/cm$^3$, and still more preferably 50 mg/cm$^3$ to 150 mg/cm$^3$.

The tap density is a value indicating how many blocks can be used to tightly fill a cell structure with a certain volume. It can be seen that a cell structure cannot be tightly filled with blocks if the value becomes smaller, that is, the structure of the blocks is complicated. It is considered that the tap density of a biocompatible macromolecular block indicates complexity of the structure of the surface of the biocompatible macromolecular block, and an amount of voids formed in a case where biocompatible macromolecular blocks are gathered as an aggregation. As the tap density becomes smaller, the voids between the macromolecular blocks are more increased and an engraftment region of cells is more increased. In addition, by maintaining the tap density not to be too small, biocompatible macromolecular blocks can moderately exist between the cells, and it is possible to deliver nutrients to the inside of a structure in a case where a cell structure for cell transplantation is set as the structure. Therefore, it is considered that the tap density falling within the above-described range is suitable.

The tap density referred in the present specification can be measured as follows. A container (hereinafter, denoted as a cap) (a cylindrical shape with a diameter of 6 mm and a length of 21.8 mm: a capacity of 0.616 cm$^3$) is prepared for the measurement. First, the mass of only the cap is measured. Thereafter, a funnel is put on the cap, and blocks are poured from the funnel so as to accumulate in the cap. After a sufficient amount of block is put, the cap portion is thrown against a hard object such as a desk 200 times to take off the funnel and level off the blocks using a spatula. The mass of the cap is measured in a state where the blocks are put by leveling off the one cap. It is possible to obtain the tap density by dividing the mass of only the blocks, which are calculated from the difference between the mass of only the cap and the mass of the blocks and the cap, by the volume of the cap.

The "square root of cross-sectional area/peripheral length" of the biocompatible macromolecular blocks in the present invention is 0.01 to 0.13, preferably 0.02 to 0.12, more preferably 0.03 to 0.115, and still more preferably 0.05 to 0.09.

It is considered that the "square root of cross-sectional area/peripheral length" of a biocompatible macromolecular block indicates complexity of the structure of the surface of the biocompatible macromolecular block, and an amount of voids formed in a case where biocompatible macromolecular blocks are gathered as an aggregation, similarly to the tap density. As the "square root of cross-sectional area/peripheral length" becomes smaller, the voids between the macromolecular blocks are more increased and an engraftment region of cells is more increased. In addition, by maintaining the "square root of cross-sectional area/peripheral length" not to be too small, biocompatible macromolecular blocks can moderately exist between the cells, and it is possible to deliver nutrients to the inside of a structure in a case where a cell structure for cell transplantation is set as the structure. Therefore, it is considered that the "square root of cross-sectional area/peripheral length" falling within the above-described range is suitable.

The "square root of cross-sectional area/peripheral length" of a biocompatible macromolecular block in the two-dimensional cross-sectional image can be obtained by checking the cross-sectional structure by producing a sample of the cross section of the biocompatible macromolecular block. For example, first, the cross-sectional structure of the biocompatible macromolecular block is prepared as a sliced sample (for example, a HE dyed sample). At this time, only the biocompatible macromolecular block may be observed, or the cross-sectional structure may be observed as a cell structure containing biocompatible macromolecular blocks and cells. Regarding one biocompatible macromolecular block, a cross-sectional area and a peripheral length thereof are obtained, and then, the "square root of cross-sectional area/peripheral length" is calculated. In this manner, it is possible to obtain the "square root of cross-sectional area/peripheral length" as an average value by measuring a plurality of biocompatible macromolecular blocks which are greater than or equal to 10 biocompatible macromolecular blocks.

The size of one biocompatible macromolecular block in the present invention is not particularly limited, but is preferably 1 µm to 700 µm, more preferably 10 µm to 700 µm, still more preferably 10 µm to 300 µm, still more preferably 20 µm to 200 µm, still more preferably 20 µm to 150 µm, and particularly preferably 25 µm to 106 µm. In addition, the size of one biocompatible macromolecular block in the present invention is also preferably 50 µm to 120 µm. It is possible to achieve more excellent angiogenesis by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used when dividing the block. For example, blocks remaining on a sieve with 106 μm when blocks which have been passed through a sieve with 180 μm for sifting are sifted using the sieve with 106 μm can be regarded as blocks having a size of 106 to 180 μm. Next, blocks remaining on a sieve with 53 μm when blocks which have been passed through the sieve with 106 μm for sifting are sifted using the sieve with 53 μm can be regarded as blocks having a size of 53 to 106 μm. Next, blocks remaining on a sieve with 25 μm when blocks which have been passed through the sieve with 53 μm for sifting are sifted using the sieve with 25 μm can be regarded as blocks having a size of 25 to 53 μm.

(1-5) Method for Producing Biocompatible Macromolecular Block

The method for producing a biocompatible macromolecular block is not particularly limited as long as it is possible to obtain a biocompatible macromolecular block which satisfies the conditions described in the above-described (1-4). For example, it is possible to make the biocompatible macromolecular block be a granule form obtained by grinding a porous body of biocompatible macromolecules using a grinder (such as NEW POWERMILL). Accordingly, it is possible to obtain the biocompatible macromolecular block which satisfies the conditions described in the above-described (1-4).

In a case where a material at a 1 mm angle is prepared, it is possible to preferably use a material having a plurality of "hollow holes at 10 μm to 500 μm" in the inside of a main body and a material in which the volume of the hollow holes occupied in the main body thereof is greater than or equal to 50%, as "porous bodies" in the present invention. In these materials, the internal hollow holes may communicate with each other, or some or all of the hollow holes may be open to the surfaces of the materials.

When producing a porous body of biocompatible macromolecules, shape of ice to be formed becomes a spherical shape due to inclusion of a freezing step in which the liquid temperature (highest internal liquid temperature) in a portion having the highest liquid temperature within a solution becomes lower than or equal to a temperature which is 3° C. lower than a melting point of a solvent (a "melting point of a solvent−3° C.") in an unfrozen state. A porous body having spherical isotropic hollow holes (spherical holes) is obtained when the ice is dried through this step. The shape of the ice to be formed becomes a columnar or tabular shape in a case where the ice is frozen without including a freezing step in which the liquid temperature (highest internal liquid temperature) in a portion having the highest liquid temperature within a solution becomes higher than or equal to a temperature which is 3° C. lower than a melting point of a solvent (a "melting point of a solvent−3° C.") in an unfrozen state. A porous body having columnar or tabular hollow holes (columnar or tabular holes) which are uniaxially or biaxially long is obtained in a case where the ice is dried through this step.

In the present invention, as the shapes of hollow holes which the porous body has, spherical holes are more preferable than columnar or tabular holes. In addition, the proportion of the spherical holes occupied in the hollow holes is still more preferably greater than or equal to 50%.

In the present invention, it is preferable that it is possible to produce a porous body of biocompatible macromolecules through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature (a "melting point of a solvent−3° C.") which is 3° C. lower than a melting point of a solvent in an unfrozen state; and a step (b) of freeze-drying the frozen biocompatible macromolecules which have been obtained in the above-described step (a). This is because, according to the above-described step, it is possible to make the proportion of the spherical holes in the hollow holes be greater than or equal to 50%.

It is preferable that it is possible to make the present invention include the step (c) of grinding a porous body which has been obtained in the above-described step (b).

It is more preferable that it is possible to freeze the solution of the biocompatible macromolecules through freezing treatment in which the highest internal liquid temperature, which is a liquid temperature in a portion having the highest liquid temperature within the solution, becomes lower than or equal to a temperature ("melting point of a solvent−7° C.") which is 7° C. lower than a melting point of a solvent in an unfrozen state, in the above-described step (a). This is because, according to the above-described step, it is possible to make the proportion of the spherical holes in the hollow holes be greater than or equal to 80%.

The average hollow hole size of the hollow holes which the porous body has can be obtained through observing the cross-sectional structure of the above-described porous body. First, a cross-sectional structure of a porous body is prepared as a sliced sample (for example, a Hematoxylin-Eosin (HE) dyed sample). Thereafter, a clear projection portion inside a wall formed of macromolecules is connected to the closest projection portion and hollow holes are clarified. The thus obtained area of individual hollow holes which have been divided is measured, and then, the circle diameter in a case where the above-described area is converted into a circle is calculated. The average value of 20 or more sizes of the hollow holes can be set as the average size of hollow holes after setting the obtained circle diameter as a hollow hole size.

The space occupancy rate of a certain hollow hole size in the present specification refers to a proportion of how much volume is occupied by hollow holes having a certain hollow hole size in a porous body. Specifically, the space occupancy rate can be obtained as a proportion by dividing the area, occupied by the hollow holes having a certain hollow hole size, by the total area, from a two-dimensional cross-sectional image. In addition, it is possible to use a cross-sectional image having an exact size of 1.5 mm as the cross-sectional image to be used.

The space occupancy rate occupied by 20 μm to 200 μm of a hollow hole size of a porous body is preferably 83% to 100%, more preferably 85% to 100%, still more preferably 90% to 100%, and particularly preferably 95% to 100%.

The space occupancy rate occupied by 30 μm to 150 μm of a hollow hole size of a porous body is preferably 60% to 100%, more preferably 70% to 100%, still more preferably 80% to 100%, and particularly preferably 90% to 100%.

The space occupancy rate occupied by 20 μm to 200 μm of hollow hole sizes of a porous body and the space occupancy rate occupied by 30 μm to 150 μm of hollow hole sizes of a porous body indicate that the hollow hole size distribution in the porous body falls within a predetermined range. That is, in a case where macromolecular blocks having large sizes of 20 µm to 200 µm are used in macromolecular blocks obtained by grinding the above-described porous body, the above-described hollow hole size is a size close to the size of one macromolecular block. As a result, the structure of the macromolecular block after the grinding becomes complicated in a porous body in which the proportion of the above-described hollow hole size is large, and as a result, the complicated structure results in decrease in the tap density or the "square root of cross-sectional area/ peripheral length".

With respect to the shape of a hollow hole, a major axis and a minor axis of an individual hollow hole are obtained to calculate "major axis/minor axis" therefrom. It is possible to set a case where the "major axis/minor axis" is 1 to 2 as a spherical hole and to set a case where the "major axis/ minor axis" is greater than or equal to 3 as a columnar or tabular hole.

The porosity of the porous body in the present invention can be obtained through "porosity (P)=1−ρ/ρc (%) using a bulk density (ρ) and a true density (ρc). The bulk density (ρ) can be calculated from dry mass and volume, and the true density (ρc) can be obtained through Hubbard pycnometry. The porosity of the macromolecular porous body in the present invention is preferably 81% to 99.99% and more preferably 95.01% to 99.9%.

(2) Cell

As cells used in the present invention, it is possible to use arbitrary cells as long as treatment of brain damage can be performed, and the kinds thereof are not particularly limited. In addition, one kind of cell may be used or a plurality of kinds of cells may be used in combination. In addition, cells to be used are preferably animal cells, more preferably vertebrate animal-derived cells, and particularly preferably human-derived cells. The kinds of vertebrate animal-derived cells (particularly human-derived cells) may be any one of pluripotent cells, somatic stem cells, precursor cells, and mature cells. As the pluripotent cells, it is possible to use, for example, embryonic stem (ES) cells, germline stem (GS) cells, or induced pluripotent stem (iPS) cells. As the somatic stem cells, it is possible to use, for example, mesenchymal stem cells (MSC), hematopoietic stem cells, amniotic cells, cord blood cells, bone marrow cells (bone marrow-derived cells), cardiac muscle stem cells, adipose-derived stem cells, or neural stem cells. As the precursor cells and mature cells, it is possible to use, for example, cells derived from nerves, the brain, or bone marrow. As the human-derived cells, it is possible to use, for example, ES cells, iPS cells, MSC, nerve cells, vascular endothelial cells, bone marrow-derived cells, or hematopoietic stem cells. In addition, the cells may be derived from any one of autologous cells and heterologous cells. For example, cells which can be differentiated into neuronal precursor cells or nerve cells can be administered with respect to cerebral ischemia or cerebral infarction.

In addition, it is possible to use vascular cells. In the present specification, the vascular cells mean cells associated with angiogenesis, and are cells constituting blood vessels and blood, and precursor cells and somatic stem cells which can be differentiated to the cells thereof. Here, pluripotent cells such as ES cells, GS cells, or iPS cells; or cells, such as mesenchymal stem cells (MSC), constituting blood vessels and blood, which are not naturally differentiated are not contained in the vascular cells. As the vascular cells, cells constituting blood vessels are preferable. In the vertebrate animal-derived cells (particularly human-derived cells), specific examples of the cells constituting blood vessels include vascular endothelial cells and vascular smooth muscle cells. As the vascular endothelial cells, any of venous endothelial cells and arterial endothelial cells may be used. As the precursor cells of the vascular endothelial cells, it is possible to use vascular endothelial precursor cells, and to preferably use vascular endothelial cells and vascular endothelial precursor cells. As the cells constituting blood, it is possible to use corpuscle cells. It is possible to use white corpuscle cells such as lymphocytes or neutrophils, monocyte cells, and hematopoietic stem cells which are stem cells thereof.

In the present specification, the non-vascular cells mean cells other than the above-described vascular cells. For example, ES cells, iPS cells, mesenchymal stem cells (MSC), or nerve cells can be used. MSC or iPS cells can be preferably used. MSC is more preferably used.

As the cells used in the present invention, it is possible to use cells in which a nervous system gene is expressed and to preferably use MSC in which a nervous system gene is expressed.

Examples of the nervous system gene include Sox2, Nestin, NeuroD1 (Neurogenic differentiation 1), GAD1 (GABA synthesis), GRIA1 (glutamate receptor 1), GRIA2 (glutamate receptor 2), CHRM1 (acetylcholine receptor 1), GABRA1 (GABAA receptor α1), GABBR1 (GABAB receptor 1), CHAT (acetylcholine synthesis), DDC (serotonin/DOPA synthesis), HTR1A (cerotonin receptor 1A), HTR1B (cerotonin receptor 1B), HTR2A (cerotonin receptor 2A), 5-HTT (cerotonin transporter), Ascl1 (neural stem cell neuron differentiation marker), Hes1 (neural stem cell astrocyte differentiation marker), and Olig2 (neural stem cell oligodendrocyte differentiation marker), but are not particularly limited thereto. As the cells used in the present invention, it is possible to use cells (preferably MSC) in which one or more kinds among the above-described nervous system genes, preferably two or more kinds thereof, more preferably three or more kinds thereof, still more preferably five or more kinds thereof, still more preferably seven or more kinds thereof, particularly preferably ten or more kinds thereof, or most preferably 13 kinds or more kinds thereof are expressed.

For example, it is possible to use cells (preferably MSC) in which one or more kinds among the genes selected from Sox2, Nestin, NeuroD1, GAD1, GRIA1, GRIA2, GABRA1, GABBR1, DDC, HTR1B, HTR2A, 5-HTT, and Hes1, preferably two or more kinds thereof, more preferably three or more kinds thereof, still more preferably five or more kinds thereof, still more preferably seven or more kinds thereof, particularly preferably ten or more kinds thereof, or most preferably all of 13 kinds thereof are expressed. However, in the present invention, it is also possible to use MSC in which the above-described genes are not expressed or MSC in which nervous system genes other than the above-described genes are expressed.

The method for measuring the expression state (presence and absence of expression and degree of expression) of particular genes in cells is well known to those skilled in the art, and it is possible to measure the expression state through a usual method such as a reverse transcription polymerase chain reaction (RT-PCR) or Northern blotting.

(3) Cell Structure for Brain Damage Treatment

In the present invention, the cell structure can have a thickness suitable for cell transplantation by three-dimensionally arranging a plurality of biocompatible macromolecular blocks in gaps between a plurality of cells in a mosaic shape using the biocompatible macromolecular blocks and the cells. Furthermore, a cell structure in which cells evenly exist in the structure is formed by three-dimensionally arranging the biocompatible macromolecular blocks and the cells in a mosaic shape, and it is possible to deliver nutrients to the inside of the cell structure from the outside. Accordingly, if cell transplantation is performed using the cell structure for brain damage treatment of the present invention, it is possible to perform transplantation while suppressing necrosis of the transplanted cells. The "suppressing of necrosis" referred to herein means that the degree of necrosis is lower than that in a case where only cells, not being a cell structure, are transplanted.

In the cell structure for brain damage treatment of the present invention, the plurality of biocompatible macromolecular blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through biocompatible macromolecular blocks, that is, the gap distance when selecting a certain cell, and a cell existing in a shortest distance from the certain cell is not particularly limited. However, the distance is preferably the size of a biocompatible macromolecular block, and a favorable distance is also within the range of the favorable size of a biocompatible macromolecular block.

In addition, the biocompatible macromolecular blocks have a configuration of being interposed by the cells. However, there are not necessarily cells between all of the biocompatible macromolecular blocks, and there may be a place where biocompatible macromolecular blocks are brought into contact with each other. The distance between biocompatible macromolecular blocks through cells, that is, the distance when selecting a biocompatible macromolecular block, and a biocompatible macromolecular block existing in a shortest distance from the biocompatible macromolecular block is not particularly limited. However, the distance is preferably the size of an aggregation of cells when one or several cells to be used are gathered. For example, the size thereof is 10 µm to 1000 µm, preferably 10 µm to 100 µm, and more preferably 10 µm to 50 µm.

The expressions such as "evenly exist", for example, the "cell structure in which cells evenly exist in the structure" are used in the present specification. However, the expression does not mean complete evenness, but means that it is possible to deliver nutrients to the inside of the cell structure from the outside and to prevent necrosis of transplanted cells.

The thickness or the diameter of the cell structure for brain damage treatment can be set to a desired thickness. As the lower limit, being greater than or equal to 215 µm is preferable, being greater than or equal to 400 µm is more preferable, and being greater than or equal to 730 µm is most preferable. The upper limit of the thickness or the diameter is not particularly limited, but a general range in use is preferably less than or equal to 3 cm, more preferably less than or equal to 2 cm, and still more preferably less than or equal to 1 cm. In addition, the range of the thickness or the diameter of the cell structure for brain damage treatment is preferably 400 µm to 3 cm, more preferably 500 µm to 2 cm, and still more preferably 720 µm to 1 cm. By setting the thickness or the diameter of the cell structure for brain damage treatment to be within the above-described range, it is possible to further promote angiogenesis.

In the cell structure for brain damage treatment of the present invention, a region formed of biocompatible macromolecular blocks and a region formed of cells are preferably arranged in a mosaic shape. The "thickness or the diameter of cell structure for brain damage treatment" in the present specification indicates the following. In a case where selecting a certain point A in the cell structure, the length of a line segment which divides the cell structure is set as a line segment A such that the distance from the external boundary of the cell structure becomes shortest within a straight line passing through the point A. A point A at which the line segment A thereof in the cell structure becomes longest is selected, and the length of the line segment A during the selection thereof is set as the "length or the diameter of the cell structure for brain damage treatment".

In the cell structure for brain damage treatment of the present invention, the ratio of a biocompatible macromolecular block to a cell is not particularly limited. However, the ratio of a biocompatible macromolecular block per cell is preferably 0.0000001 µg to 1 µg, more preferably 0.000001 µg to 0.1 µg, still more preferably 0.00001 µg to 0.01 µg, and most preferably 0.00002 µg to 0.006 µg. By setting the ratio of the biocompatible macromolecular block to the cell to be within the above-described range, it is possible to make the cells more evenly exist. By setting the lower limit to be within the above-described range, it is possible to exhibit an effect of the cells when using the cells for the above-described purpose. Moreover, by setting the upper limit to be within the above-described range, it is possible to supply components in arbitrarily existing biocompatible macromolecular blocks to cells. Here, the components in biocompatible macromolecular blocks are not particularly limited, but examples thereof include components contained in a medium to be described below.

In addition, the cell structure for brain damage treatment of the present invention may contain an angiogenic factor. Here, examples of the angiogenic factor favorably include a basic fibroblast growth factor (bFGF), a vascular endothelial growth factor (VEGF), and a hepatocyte growth factor (HGF). The method for producing a cell structure containing an angiogenic factor is not particularly limited, but examples thereof include a production method using biocompatible macromolecular blocks in which an angiogenic factor is impregnated. It is preferable that the cell structure for brain damage treatment of the present invention contains an angiogenic factor from the viewpoint of promoting angiogenesis.

The cell structure for brain damage treatment of the present invention may contain non-vascular cells. In addition, cells constituting the cell structure may be only non-vascular cells. It is possible to form blood vessels in a transplantation site after the transplantation using the cell structure which contains only non-vascular cells as cells. In addition, in a case where the cells constituting the cell structure are two or more kinds and include both of non-vascular cells and vascular cells, it is possible to form more blood vessels compared to the case where the cell structure is constituted of only non-vascular cells, which is preferable.

A cell structure in which blood vessels are formed is also preferable as the cell structure for brain damage treatment of the present invention.

A cell structure in which blood vessels are formed using the cell structure which contains two or more kinds of cells and contains both non-vascular cells and vascular cells is also included in the cell structure for brain damage treatment of the present invention.

(4) Method for Producing Cell Structure for Brain Damage Treatment

The cell structure for brain damage treatment of the present invention can be produced by mixing a biocompatible macromolecular block with at least one kind of cell.

More specifically, the cell structure for brain damage treatment of the present invention can be produced by alternately arranging a biocompatible macromolecular block and a cell. The production method is not particularly limited, but a method for sowing cells after forming a biocompatible macromolecular block is preferably used. Specifically, it is possible to produce the cell structure for brain damage treatment of the present invention by incubating a mixture of a biocompatible macromolecular block and a cell-containing culture solution. For example, in the solution held by a container, in the container, a cell and the previously produced biocompatible macromolecular block are arranged in a mosaic shape. It is preferable to promote or control the formation of the arrangement, which is formed of a cell and a biocompatible base material, in a mosaic shape, through natural aggregation, natural fall, centrifugation, or agitation as means for the arrangement.

According to the present invention, there is provided a method for producing the cell structure for brain damage treatment, the method comprising: a step of mixing cells and biocompatible macromolecular blocks of which the tap density is 10 mg/cm$^3$ to 500 mg/cm$^3$ or a value obtained by dividing a square root of a cross-sectional area in a two-dimensional cross-sectional image by a peripheral length is 0.01 to 0.13, and culturing the mixture for 10 hours or longer. That is, a cell structure for brain damage treatment of the present invention which has been obtained by mixing cells and biocompatible macromolecular blocks and culturing the mixture for 10 hours or longer is preferable, a cell structure for brain damage treatment of the present invention which has been obtained by mixing cells and biocompatible macromolecular blocks and culturing the mixture for 12 hours or longer is more preferable, a cell structure for brain damage treatment of the present invention which has been obtained by mixing cells and biocompatible macromolecular blocks and culturing the mixture for 15 hours or longer is still more preferable, a cell structure for brain damage treatment of the present invention which has been obtained by mixing cells and biocompatible macromolecular blocks and culturing the mixture for 18 hours or longer is most preferable. After mixing the cells and the biocompatible macromolecular blocks, it is preferable to culture the mixture for the above-described hours without performing centrifugation.

As the container to be used, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape.

In the cell structure (mosaic cell aggregation) obtained through the above-described method, it is possible to produce a cell structure having a desired size through a method, for example,
(a) merging cell structures (mosaic cell aggregations), which have been separately prepared, with each other, or
(b) increasing the volume of the structure under a differentiation medium or a proliferation medium.

The method for merging the cell structures with each other or the method for increasing the volume of the cell structure is not particularly limited.

For example, it is possible to increase the volume of the cell structure by exchanging a medium with a differentiation medium or a proliferation medium in a step of incubating a mixture of a biocompatible macromolecular block and a cell-containing culture solution. Preferably, it is possible to produce a cell structure in which cells evenly exist in the cell structure and which has a desired size, by further adding a biocompatible macromolecular block, in the step of incubating a mixture of a biocompatible macromolecular block and a cell-containing culture solution.

In a case where cell structures which have been separately prepared are merged with each other, it is possible to, for example, merge a plurality of cell structures which contains a plurality of biocompatible macromolecular blocks and a plurality of cells and in which one or a plurality of the above-described biocompatible macromolecular blocks are arranged in some or all of a plurality of gaps formed by the plurality of the above-described cells. A cell structure obtained by merging a plurality of cell structures with each other as described in the above-described (a) can also be used as the cell structure for brain damage treatment of the present invention.

Favorable ranges of the "(kinds, sizes, or the like) of biocompatible macromolecular blocks", the "cells", the "gaps between the cells", the "(size or the like) of the obtained cell structure", the "ratio of the cells to the biocompatible macromolecular blocks", and the like in the method for producing a cell structure for brain damage treatment of the present invention are the same as those described above in the present specification.

The thickness or the diameter of each cell structure before the above-described merging is preferably 10 μm to 1 cm, more preferably 10 μm to 2000 μm, still more preferably 15 μm to 1500 μm, and most preferably 20 μm to 1300 μm. The thickness or the diameter thereof after the merging is preferably 400 μm to 3 cm, more preferably 500 μm to 2 cm, and still more preferably 720 μm to 1 cm.

Specific examples of the above-described method for producing a cell structure having a desired size by further adding a biocompatible macromolecular block include a method for performing incubating after further adding a second biocompatible macromolecular block to a cell structure which contains a plurality of first biocompatible macromolecular blocks and a plurality of cells and in which one or a plurality of the above-described biocompatible macromolecular blocks are arranged in some or all of a plurality of gaps formed by the plurality of the above-described cells. Here, favorable ranges of the "(kinds, sizes, or the like) of biocompatible macromolecular blocks", the "cells", the "gaps between the cells", the "(size or the like) of the obtained cell structure", the "ratio of the cells to the biocompatible macromolecular blocks", and the like are the same as those described above in the present specification.

Cell structures which need to be merged with each other are preferably installed in a distance of 0 to 50 μm, more preferably installed in a distance of 0 to 20 μm, and still more preferably installed in a distance of 0 to 5 μm. It is considered that, when merging cell structures with each other, cells or a substrate produced by the cells play a role of an adhesive due to proliferation and extension of cells, and the cell structures are bonded to each other. Therefore, it is easy to bond the cell structures to each other by making the distance thereof be within the above-described range.

The range of the thickness or the diameter of the cell structure obtained in the above is preferably 400 μm to 3 cm, more preferably 500 μm to 2 cm, and still more preferably 720 μm to 1 cm.

It is preferable to appropriately select pace for further adding a second biocompatible macromolecular block to a cell structure when performing incubating after further adding the second biocompatible macromolecular block to the cell structure in accordance with the proliferation rate of cells to be used. Specifically, if the pace for adding a second biocompatible macromolecular block is fast, cells move to the outside of a cell structure, and therefore, the evenness of the cells is deteriorated. If the pace for adding the second biocompatible macromolecular block is slow, a place in which the proportion of cells is increased can be generated, and therefore, evenness of the cells is deteriorated. Thus, the pace is selected in consideration of the proliferation rate of cells to be used.

Favorable examples of the method for producing a cell structure in a case of containing both of the non-vascular cells and vascular cells include the following production methods (a) to (c).

(a) is a production method including a step of adding a vascular cell and a biocompatible macromolecular block after forming a cell structure through the above-described method using a non-vascular cell. Here, the "step of adding a vascular cell and a biocompatible macromolecular block" includes all of the above-described method for merging cell structures (mosaic cell aggregations), which have been prepared, with each other and the above-described method for increasing the volume of the structure under a differentiation medium or a proliferation medium.

(b) is a production method including a step of adding a non-vascular cell and a biocompatible macromolecular block after forming a cell structure through the above-described method using a vascular cell. Here, the "step of adding a non-vascular cell and a biocompatible macromolecular block" includes all of the above-described method for merging cell structures (mosaic cell aggregations), which have been prepared, with each other and the above-described method for increasing the volume of the structure under a differentiation medium or a proliferation medium.

(c) is a production method in which a cell structure is formed through the above-described method using non-vascular cells and vascular cells substantially at the same time.

(5) Use of Cell Structure for Treating Brain Damage, Brain Damage Treatment Agent, and Method for Treating Brain Damage The above-described cell structure can be used for treating brain damage. That is, the present invention provides a cell structure for use in treatment of brain damage, and a brain damage treatment agent containing the above-described cell structure.

Brain damage widely means a state in which damage is caused to the function of the brain. Examples thereof include brain injury, hypoxic-ischemic brain damage, cerebral infarction, and/or cerebral stroke, but are not limited thereto.

A route of administration of the cell structure for brain damage treatment and the brain damage treatment agent of the present invention is not particularly limited, and may be systemic administration (parenteral administration or the like) or local administration (for example, transplantation into a treatment site). The administration of the cell structure for brain damage treatment or the brain damage treatment agent of the present invention can be performed through various methods, for example, through injection thereof via an injection cannula, a needle, or a shunt, but is not limited thereto. In a case where the cell structure for brain damage treatment or the brain damage treatment agent of the present invention is systemically administered, parenteral administration, for example, intravenous administration, intraarterial administration, intramuscular administration, intracutaneous administration, or subcutaneous administration is preferable. The cell structure for brain damage treatment or the brain damage treatment agent of the present invention can be locally administered to a treatment site (a disease site, for example, a lesion site of the brain). A benefit of the local administration is that it is possible to more accurately target cells at a lesion site. The local administration is more preferable.

In a case where the cell structure for brain damage treatment or the brain damage treatment agent of the present invention is transplanted into a lesion site of the brain, it is possible to perform the transplantation through stereotactic surgery. In this case, a patient is anesthetized. The head of the patient is placed in a magnetic resonance image (MRI)-compatible stereotactic frame, and a micropositioner having a microinjector is disposed on the skull. It is possible to make a burr hole on the cranial bone of the patient using a dental drill or other appropriate tools in order to expose the dura mater immediately above a target site.

The number of cells in the cell structure for brain damage treatment and the brain damage treatment agent of the present invention can be set to the number of cells which has been calculated so as to produce a predetermined treatment effect. The number of cells per administration of the cell structure for brain damage treatment and the brain damage treatment agent of the present invention is preferably about $1.0 \times 10^4$ to $5.0 \times 10^7$ pieces/kg body weight per 1 kg of the body weight of a patient, more preferably about $1.0 \times 10^5$ to $1.0 \times 10^7$ pieces/kg body weight per 1 kg of the body weight of a patient, still more preferably about $1.0 \times 10^6$ to $6.0 \times 10^6$ pieces/kg body weight per 1 kg of the body weight of a patient.

In addition, according to the present invention, there is provided a method for treating brain damage, the method comprising: a step of administering the above-described cell structure for brain damage treatment of the invention to a patient with brain damage. The favorable ranges of the administration method and the cell structure are the same as those described above.

Furthermore, according to the present invention, there is provided use of the above-described cell structure for brain damage treatment of the present invention for producing a brain damage treatment agent. The favorable ranges of the brain damage treatment agent and the cell structure are the same as those described above.

The present invention will be more specifically described using the following Examples, but is not limited by Examples.

EXAMPLE

[Example 1] Recombinant Peptide (Recombinant Gelatin)

CBE3 (which is disclosed in WO2008/103041A) described in the following was prepared as recombinant peptides (recombinant gelatin).
CBE3
Molecular weight: 51.6 kD
Structure: GAP[(GXY)$_{63}$]$_3$G
Number of amino acids: 571
RGD sequence: 12
Imino acid content: 33%

Almost 100% of amino acids have a repeating structure of GXY. In the amino acid sequence of CBE3, serine, threonine, asparagine, tyrosine, and cysteine are not included.
CBE3 has an ERGD sequence.
Isoelectric point: 9.34, GRAVY value: −0.682, 1/IOB value: 0.323

Amino acid sequence (SEQ ID No: 1 in a sequence table) (which is the same as that of SEQ ID No: 3 in WO2008/103041A. However, X in the end is corrected to "P").

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G

[Example 2] Production of Porous Body (Macromolecular Porous Body) of Recombinant Peptide A cylindrical cup-shaped aluminum container with a thickness of 1 mm and a diameter of 47 mm was prepared. When the curved surface of the cylindrical cup is set as a side surface, the side surface of the cylindrical cup is closed by aluminum with 1 mm and the bottom surface (circular shape of a flat plate) is also closed by aluminum with 1 mm. In contrast, the upper surface is in an open shape. In addition, TEFLON (registered trademark) with a thickness of 1 mm is evenly spread over only the inside of the side surface, and as a result, the inner diameter of the cylindrical cup became 45 mm. Hereinafter, this container is referred to as a cylindrical container.

An aqueous CBE3 solution was prepared and was made to flow into the cylindrical container. The aqueous CBE3 solution was cooled down from the bottom surface within a freezer using a cooling shelf. At this time, the temperature of the cooling shelf, the thickness of a heat insulating plate (glass) which was interposed between the shelf and the cylindrical container, the final concentration of the aqueous CBE3 solution to be put, and the amount of aqueous solution were prepared as described below.
Condition a: the temperature of the shelf being −40° C., the thickness of the glass being 2.2 mm, the final concentration of the aqueous CBE3 solution being 12 mass %, and the amount of aqueous solution being 4 mL.
Condition b: the temperature of the shelf being −60° C., the thickness of the glass being 2.2 mm, the final concentration of the aqueous CBE3 solution being 7.5 mass %, and the amount of aqueous solution being 4 mL.
Condition c: the temperature of the shelf being −40° C., the thickness of the glass being 2.2 mm, the final concentration of the aqueous CBE3 solution being 4.0 mass %, and the amount of aqueous solution being 4 mL.
Frozen CBE3 blocks which have been obtained in this manner were freeze-dried to obtain CBE3 porous bodies.

[Comparative Example 1] Production of Simply Frozen Porous Body of Recombinant Peptide 2000 mg of CBE3 was dissolved in 18 mL of ultrapure water at 50° C. to produce 20 mL of a CBE3 solution with a final concentration of 10 mass %. Thin plate-shaped gel with a thickness of about 4 mm was produced by thinly spreading the CBE3 solution. A container in which a white plate was put into a silicon frame (about 5 cm×10 cm) which was pressed on the white plate so as not to make an air gap is used. Then, the above-described CBE3 solution (50° C.) was made to flow into the above-described frame. Gelation was performed about 1 hour while shifting the temperature to 4° C. after the flowing of the solution. After checking solidification of the solution, the temperature was shifted to −80° C. to freeze the gel for 3 hours. After the freezing, freeze-drying was performed using a freeze dryer (EYELA, FDU-1000). The obtained freeze-dried body was a porous body and the average pore size became 57.35 µm. Hereinafter, this is referred to as a simply frozen porous body.

[Example 3] Evaluation of Hollow Hole Size and Space Occupancy Rate of Porous Body of Recombinant Peptide Evaluation of the hollow hole size and the space occupancy rate of a porous body was performed on the CBE3 porous bodies obtained in Example 2 and the simply frozen porous body obtained in Comparative Example 1. After the obtained porous bodies were subjected to thermal cross-linking for 20 hours at 160° C. and were made insoluble, the porous bodies were swelled with a physiological salt solution for sufficient time. Thereafter, a frozen tissue piece was produced using a microtome, and a Hematoxylin-Eosin (HE) dyed sample was produced. A cross-sectional image having a large size of 1.5 mm of a real scale was prepared from the sample, the areas of individual hollow holes were measured. Thereafter, the circle diameter in a case where the above-described area was converted into a circle was calculated and was set as a hollow hole size. The average value of 20 or more sizes of the hollow holes was set as the average size of hollow holes. As a result, the porous body under the condition a had a size of 66.39 µm, the porous body under the condition b had a size of 63.17 µm, and the porous body under the condition c had a size of 56.36 µm.

Specifically, the space occupancy rate can be obtained as a proportion by dividing the area, occupied by the hollow holes having certain hollow hole sizes, by the total area, from a two-dimensional cross-sectional image based on the calculated hollow hole sizes. As a result, the space occupancy rate of 20 µm to 200 µm of hollow holes in the CBE3 porous bodies obtained in Example 2 was 100% in the porous body under the condition a, 99.9% in the porous body under the condition b, and 99.9% in the porous body under the condition c. The space occupancy rate of 30 µm to 150 µm of hollow holes was 94.2% in the porous body under the condition a, 97.9% in the porous body under the condition b, and 99.3% in the porous body under the condition c.

In contrast, in the simply frozen porous body obtained in Comparative Example 1, the sizes of the hollow holes greatly varied, and there was a place where hollow holes having large sizes were gathered and a place where hollow holes having small sizes were gathered. In the place with hollow holes having large sizes, the space occupancy rate of 20 µm to 200 µm of hollow holes was 74.3% and the space occupancy rate of 30 µm to 150 µm of hollow holes was 55.8%. In the place with hollow holes having small sizes, the space occupancy rate of 20 µm to 200 µm of hollow holes was 82.8% and the space occupancy rate of 30 µm to 150 µm of hollow holes was 57.2%. If the place with hollow holes having large sizes and the place with hollow holes having small sizes were mixed to each other half by half, the space occupancy rate of 20 µm to 200 µm of hollow holes became 78.6% and the space occupancy rate of 30 µm to 150 µm of hollow holes became 56.5% (FIG. 6).

[Example 4] Measurement of Porosity of Porous Body of Recombinant Peptide

The porosity of the CBE3 porous bodies obtained in Example 2 was measured. When measuring the porosity, a bulk density ($\rho$) and a true density ($\rho c$) were measured to obtain the porosity ($P=1-\rho/\rho c$ (%)). The bulk density ($\rho$) of the CBE3 porous bodies was calculated from dry mass and volume. The true density ($\rho c$) was obtained through Hubbard pycnometry. As a result of the number of samples (N) being 4, it became clear that, in the porous body under the condition c, the bulk density was 0.05 g/cm$^3$ and the true density was 1.23 g/cm$^3$, and the porosity was 96% (a value of coefficient of variation (CV) was 8%). In addition, it was found that the porosity in the respective porous bodies under the conditions a and b was 87% (the CV value was 10%) and 92% (the CV value was 7%).

[Example 5] Production of Recombinant Peptide Block (Grinding and Cross-Linking of Porous Body)

The CBE3 porous bodies under the conditions a, b, and c obtained in Example 2 were ground using NEW POWERMILL (Osaka Chemical Co., Ltd., NEW POWERMILL PM-2005). The grinding was performed for one minute×5 times, that is, for 5 minutes in total at the maximum rotation speed. The obtained ground substance was divided according to the size using a stainless steel sieve to obtain CBE3 blocks at 25 to 53 µm, 53 to 106 µm, and 106 µm to 180 µm. Thereafter, samples were obtained by performing thermal cross-linking (the cross-linking was performed for 9 kinds of cross-linking time including 24 hours, 48 hours, 56 hours, 60 hours, 72 hours, 84 hours, 96 hours, 120 hours, and 288 hours) at 160° C. under reduced pressure. Hereinafter, 53 to 106 µm under the condition a was called "12% being middle", 25 to 53 µm under the condition b was called "7.5% being small", 53 to 106 µm under the condition b was called "7.5% being middle", 106 to 180 µm under the condition b was called "7.5% being large", and 53 µm to 106 µm under the condition C was called "4% being middle".

[Comparative Example 2] Production of Cross-Linked µBlock of Glutaraldehyde (GA) of Recombinant Peptide An amorphous GA cross-linked µblock was produced as a Comparative Example, in which glutaraldehyde disclosed in JP2012-219100A was used, using recombinant peptide CBE3 as a base material. 1000 mg of CBE3 was dissolved in 9448 µL of ultrapure water and 152 µL of 1 mol/L HCL was added thereto. Then, 400 µL of 25 mass % glutaraldehyde was added thereto so as to make the final concentration be 1.0 mass %. Then, the mixture was reacted for 3 hours at 50° C. to produce cross-linked gel. This cross-linked gel was immersed in 1 L of a 0.2 M glycine solution and was shaken for 2 hours at 40° C. Thereafter, the cross-linked gel was shaken and washed in 5 L of ultrapure water for 1 hour. The ultrapure water was substituted with a new substance and was washed again for 1 hour. The washing was repeated in total 6 times. The cross-linked gel after being washed was frozen for 5 hours at −80° C., and then, freeze-drying was performed using a freeze dryer (EYELA, FDU-1000). The obtained freeze-dried body was ground using NEW POWERMILL (Osaka Chemical Co., Ltd., NEW POWERMILL PM-2005). The grinding was performed for one minute×5 times, that is, for 5 minutes in total at the maximum rotation speed. The obtained ground substance was divided according to the size using a stainless steel sieve to obtain CBE3 • GA cross-linked µblocks at 25 to 53 µm.

[Comparative Example 3] Production of Recombinant Peptide Block for Comparison

A recombinant peptide block for comparison which can be produced in a case of being produced through a step in which glutaraldehyde is not contained and which can be inferred from the related art (JP2012-219100A) was produced as described below as a comparative example. A block was produced using recombinant peptide CBE3 as a base material. The simply frozen porous body obtained in Comparative Example 1 was ground using NEW POWERMILL (Osaka Chemical Co., Ltd., NEW POWERMILL PM-2005). The grinding was performed for one minute×5 times, that is, for 5 minutes in total at the maximum rotation speed. The obtained ground substance was divided according to the size using a stainless steel sieve to obtain CBE3 blocks at 25 to 53 µm. These CBE3 blocks were placed in an oven at 160° C. and were subjected to thermal cross-linking for 72 hours.

[Example 6] Measurement of Tap Density of Recombinant Peptide Block

The tap density is a value indicating how many blocks can be used to tightly fill a cell structure with a certain volume. It can be said that a cell structure cannot be tightly filled with blocks if the value becomes smaller, that is, the structure of the blocks is complicated. The tap density was measured as follows. First, a container, to which a cap (a cylindrical shape with a diameter of 6 mm and a length of 21.8 mm: a capacity of 0.616 cm$^3$) was attached at a tip of a funnel, was prepared, and the mass of only the cap was measured. Thereafter, the cap was attached to the funnel and blocks were poured from the funnel so as to accumulate in the cap. After a sufficient amount of block was put, the cap portion was thrown against a hard object such as a desk 200 times to take off the funnel and level off the blocks using a spatula. The mass of the cap was measured in a state where the blocks were put by leveling off the one cap. It was possible to obtain the tap density by dividing the mass of only the blocks, which were calculated from the difference between the mass of only the cap and the mass of the blocks and the cap, by the volume of the cap.

As a result, the blocks in Comparative Example 2 were 715 mg/cm$^3$, the blocks in Comparative Example 3 were 524 mg/cm$^3$.

In contrast, in the blocks in Example 5, "12% being middle" was 372 mg/cm$^3$, "7.5% being small" was 213 mg/cm$^3$, "7.5% being middle" was 189 mg/cm$^3$, "7.5% being large" was 163 mg/cm$^3$, and "4% being middle" was 98 mg/cm$^3$. In the blocks in Example 5, it was found that the tap density became small with respect to the blocks in Comparative Example 3 while being derived from the complexity of the structure.

[Example 7] Calculation of "Square Root of Cross-Sectional Area/Peripheral Length" in Two-Dimensional Cross-Sectional Image of Recombinant Peptide Block The relationship between a "square root of an area" of a block and a "peripheral length" was obtained as an index indicating complexity of the block. That is, it can be said that a smaller value of the "square root of cross-sectional area/peripheral length" of the block is more complicated. This value was calculated using image analysis software. First, an image from which the shape of the block was recognized was prepared. Specifically, in this Example, a sample in which a block group well swelled with water was made into a frozen piece using microtome and was dyed with Hematoxylin-Eosin (HE)) was used. In a case where cells or the like exist besides the blocks, only blocks are remained on the image by extracting only a formulation with an automatic selection tool using Photoshop (registered trademark). In the image, the area of the block and the peripheral length were obtained using Imagej (registered trademark) to calculate a value of "square root of cross-sectional area/peripheral length". However, blocks of less than or equal to 10 μm are removed.

As a result, the blocks in Comparative Example 2 became 0.248 and the blocks in Comparative Example 3 became 0.139.

In contrast, in the blocks in Example 5, "12% being middle" was 0.112, "7.5% being small" was 0.083, "7.5% being middle" was 0.082, "7.5% being large" was 0.071, and "4% being middle" was 0.061. In the blocks in Example 5, it was found that the value of "square root of cross-sectional area/peripheral length" became small with respect to the blocks in Comparative Example 3 while being derived from the complexity of the structure and has a correlation with the tap density.

[Example 8] Production of Mosaic Cell Aggregation (hMSC) in which Recombinant Peptide Block is Used Human bone marrow-derived mesenchymal stem cells (hMSC) were adjusted to be 100000 cells/mL using a proliferation medium (TAKARA BIO INC.: MSCGM BulletKit (registered trademark)), and CBE3 blocks which had been produced in Example 5 were added thereto so as to make a concentration of 0.1 mg/mL. Then, 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the CBE3 blocks and hMSC cells and was in a spherical shape with a diameter of about 1 mm, was produced. Since this mosaic cell aggregation was produced in a U-shaped plate, the mosaic cell aggregation was in a spherical shape. In addition, it was possible to produce all of these "12% being middle", "7.5% being small", "7.5% being middle", "7.5% being large", and "4% being middle" in the same manner as in the above.

[Comparative Example 4] Production of Mosaic Cell Aggregation (hMSC) in which Recombinant Peptide Block for Comparison is Used Human bone marrow-derived mesenchymal stem cells (hMSC) were adjusted to be 100000 cells/mL using a proliferation medium (TAKARA BIO INC.: MSCGM BulletKit (registered trademark)), and CBE3 blocks which had been produced in Comparative Example 3 were added thereto so as to make a concentration of 0.1 mg/mL. Then, 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the CBE3 blocks and hMSC cells and was in a spherical shape with a diameter of about 1 mm, was produced. Since this mosaic cell aggregation was produced in a U-shaped plate, the mosaic cell aggregation was in a spherical shape.

[Comparative Example 5] Production of Mosaic Cell Aggregation (hMSC) in which Recombinant Peptide GA Cross-Linked μBlock is Used A mosaic cell aggregation containing glutaraldehyde for comparison was produced as follows. Human bone marrow-derived mesenchymal stem cells (hMSC) were adjusted to be 100000 cells/mL using a proliferation medium (TAKARA BIO INC.: MSCGM BulletKit (registered trademark)), and GA cross-linked μblocks which had been produced in Comparative Example 2 were added thereto so as to make a concentration of 0.1 mg/mL. Then, 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the GA cross-linked μblocks and hMSC cells and was in a spherical shape with a diameter of about 1 mm, was produced. Since this mosaic cell aggregation was produced in a U-shaped plate, the mosaic cell aggregation was in a spherical shape.

[Example 9] Production of Mosaic Cell Aggregations (hMSC+hECFC) in which Recombinant Peptide Block is Used Human vascular endothelial precursor cells (hECFC) were adjusted to be 100000 cells/mL using a proliferation medium (Lonza: EGM-2+ECFC serum supplement), and CBE3 blocks which had been produced in Example 5 were added thereto so as to make a concentration of 0.05 mg/mL. Then, 200 μL of the obtained mixture was sown in a Sumilon Celltight X96U plate, and the plate was centrifuged in Mini Plate Centrifuge (600 g, 5 minutes) and was allowed to stand for 24 hours to produce a flat-shaped mosaic cell aggregation formed of ECFC and the CBE3 blocks. Thereafter, the medium removed, human bone marrow-derived mesenchymal stem cells (hMSC) were adjusted to be 100000 cells/mL using a proliferation medium (TAKARA BIO INC.: MSCGM BulletKit (registered trademark)), and the CBE3 blocks which had been produced in Example 5 were added thereto so as to make a concentration of 0.1 mg/mL. Then, 200 μL of the obtained mixture containing a hECFC mosaic cell aggregation was sown in a Sumilon Celltight X96U plate, and the plate was centrifuged in Mini Plate Centrifuge (600 g, 5 minutes) and was allowed to stand for 24 hours. Accordingly, a mosaic cell aggregation which was formed of hMSC, hECFC, and the CBE3 blocks and was in a spherical shape with a diameter of about 1 mm, was produced. In addition, it was possible to produce all of these "12% being middle", "7.5% being small", "7.5% being middle", "7.5% being large", and "4% being middle" in the same manner as in the above.

[Example 10] Merging of Mosaic Cell Aggregations (hMSC) in which Recombinant Peptide Block is Used 5 mosaic cell aggregations (using CBE3 blocks for the present invention) on day 2 which had been produced in Example 8 were arranged in a Sumilon Celltight X96U plate, and culturing was performed for 24 hours. As a result, it became clear that the mosaic cell aggregations were naturally merged by bonding the mosaic cell aggregations to each other using cells which had been disposed at outer peripheral portions. In addition, it was possible to produce all of these "12% being middle", "7.5% being small", "7.5% being middle", "7.5% being large", and "4% being middle" in the same manner as in the above.

[Example 11] Merging of Mosaic Cell Aggregations (hMSC+hECFC) in which Recombinant Peptide Block is Used 5 mosaic cell aggregations (using CBE3 blocks for the present invention) on day 2 which had been produced in Example 9 were arranged in a Sumilon Celltight X96U plate, and culturing was performed for 24 hours. As a result, it became clear that the mosaic cell aggregations were naturally merged by bonding the mosaic cell aggregations to each other using cells which had been disposed at outer peripheral portions. In addition, it was possible to produce all of these "12% being middle", "7.5% being small", "7.5% being middle", "7.5% being large", and "4% being middle" in the same manner as in the above.

[Comparative Example 6] Merging of Mosaic Cell Aggregations (hMSC) in which Recombinant Peptide Block for Comparison is Used 5 mosaic cell aggregations (derived from CBE3 blocks for comparison) on day 2 which had been produced in Comparative Example 4 were arranged in a Sumilon Celltight X96U plate, and culturing was performed for 24 hours. As a result, it became clear that the mosaic cell aggregations were naturally merged by bonding the mosaic cell aggregations to each other using cells which had been disposed at outer peripheral portions.

[Comparative Example 7] Merging of Mosaic Cell Aggregation (hMSC) in which Recombinant Peptide GA Cross-Linked μBlock is Used 5 mosaic cell aggregations (derived from GA cross-linked μblocks) on day 2 which had been produced in Comparative Example 5 were arranged in a Sumilon Celltight X96U plate, and culturing was performed for 24 hours. As a result, it became clear that the mosaic cell aggregations were naturally merged by bonding the mosaic cell aggregations to each other using cells which had been disposed at outer peripheral portions.

[Example 12] In Vitro ATP Assay

The amount of adenosine triphosphate (ATP) which had been produced and held by cells in each mosaic cell aggregation was quantitatively determined. ATP is known as an energy source of all living things. By quantitatively determining an ATP synthesis amount and an ATP holding amount, it is possible to grasp a state of a metabolic activity of cells and an activity state of cells. CellTiter-Glo (Promega Corporation) was used for the measurement. Regarding the mosaic cell aggregations produced in Example 8 and Comparative Example 4 and Comparative Example 5, the ATP amount in each of the mosaic cell aggregations on day 7 was quantitatively determined using CellTiter-Glo. The result showed that the ATP amount was small in the mosaic cell aggregation in which a CBE3 block for comparison was used compared to that in the mosaic cell aggregation in which a GA cross-linked μblock was used. In contrast, it was found that the ATP amount was large in the mosaic cell aggregation in which a CBE3 block for the present invention was used compared to that in the mosaic cell aggregation in which a GA cross-linked μblock was used. This showed a result (FIG. 1) that, even in all cases of "12% being middle", "7.5% being small", "7.5% being middle", "7.5% being large", and "4% being middle", the CBE3 block for the present invention produced larger amount of ATP than the mosaic cell aggregation in which the GA cross-linked μblock is used did, in the same manner. That is, it became clear that the viable state of cells is favorable in the mosaic cell aggregation in which the CBE3 block for the present invention having a complicated structure is used.

To summarize these results, the performance is obtained at 715 mg/cm$^3$ of the tap density in the case of GA cross-linking in Comparative Example 2, but is not obtained even at 524 mg/cm$^3$ in Comparative Example 3 in which GA is not used. In contrast, from the fact that the performance is obtained at "12% being middle" being 372 mg/cm$^3$, "7.5% being small" being 213 mg/cm$^3$, "7.5% being middle" being 189 mg/cm$^3$, "7.5% being large" being 163 mg/cm$^3$, and "4% being middle" being 98 mg/cm$^3$ in Example 5, it can be seen that it is particularly important that the tap density is less than or equal to 500 mg/cm$^3$ in a case where GA is not used.

Similarly, the performance is obtained at 0.248 of the "square root of cross-sectional area/peripheral length" in the case of the GA cross-linking in Comparative Example 2, but is not obtained even at 0.139 in Comparative Example 3 in which glutaraldehyde (GA) is not used. In contrast, from the fact that the performance is obtained at "12% being middle" being 0.112, "7.5% being small" being 0.083, "7.5% being middle" 0.082, "7.5% being large" being 0.071, and "4% being middle" being 0.061 in Example 5, it can be seen that it is particularly important that the "square root of cross-sectional area/peripheral length" is less than or equal to 0.13 in a case where GA is not used.

[Example 13] Production of Giant Mosaic Cell Aggregation in which Recombinant Peptide Block is Used It is possible to produce a giant mosaic cell aggregation by merging mosaic cell aggregations with 1 mm as in Example 10. It is possible to simplify an operation if a giant mosaic cell aggregation can be produced at a time. Here, 50 mL of a 1.5 mass % agarose (Agarose S) solution was put into a 9 cm Petri dish of Sumilon Celltight which was subjected to processing in which cells are made not to be adhered thereto using a proliferation medium (TAKARA BIO INC.: MSCGM BulletKit (registered trademark)). At this time, silicon which had been made into a rod shape with 1 cm square was fixed to the agarose solution such that the silicon was immersed in the agarose solution by about 5 mm, and agarose was solidified. Then, silicon was removed, and a container in which a 1 cm square cavity was generated in agarose was prepared. A moderate amount of proliferation medium was put into the container in which gel was preserved so as not to become dry. The medium was removed, a suspended substance of 16 mg of representative blocks at "7.5% being middle" in the blocks produced in Example 5 and 2500000 human bone marrow-derived mesenchymal stem cells (hMSC) was put into the cavity, and then, 25 mL of a proliferation medium was gently added thereto. After one day of culturing, it was possible to produce a giant mosaic cell aggregation with 1 cm square and a thickness of 2 to 3 mm. This aggregation was transferred to a 9 cm Petri dish of Sumilon Celltight into which 25 mL of a proliferation medium was put. After further two days of culturing, the aggregation was transferred to a spinner flask, into which 25 mL of a proliferation medium was put, and was stirred and cultured. An HE dyed sample of a cross section of the mosaic cell aggregation after 7 days of culturing was produced. As a result, it was confirmed that cells exist in the aggregation even after 7 days of culturing. It became clear that it was possible to produce a giant mosaic cell aggregation by mixing the cells and the blocks in this manner and performing the culturing after pouring the mixture into a mold. In addition, this method can be applied to all of the GA cross-linked µblocks, the blocks for comparison, and the blocks for the present invention, and does not depend on the type of block.

[Example 14] Transplanting of Mosaic Cell Aggregation in which Recombinant Peptide Block is Used A male mouse of NOD/SCID (Charles River Laboratories International, Inc.) at the age of 4 weeks to 6 weeks was used. Body hair of the abdomen of the mouse was removed under anesthesia, a cut was made under the skin of the upper abdomen, forceps are inserted from the cut, and the skin was peeled off from the muscle. Thereafter, the mosaic cell aggregations which had been produced in Examples 10 and 11, and Comparative Examples 6 and 7 were taken out using forceps and were transplanted under the skin which was near the lower abdomen and was approximately 1.5 cm away from the cut, and the cut portion of the skin was sutured.

[Example 15] Collection of Mosaic Cell Aggregation in which Recombinant Peptide Block is Used Dissection was performed 1 week and 2 weeks after the transplantation. The skin of the abdomen was peeled off and the skin to which mosaic cell aggregations were adhered was cut off in a square shape with a size of about 1 square cm. In a case where the mosaic cell aggregations were adhered also to the muscle of the abdomen, the muscle was also collected together with the mosaic cell aggregations.

[Example 16] Analysis of Samples

Tissue pieces with respect to a skin piece to which mosaic cell aggregations were adhered and with respect to mosaic cell aggregations before transplantation were produced. The tissue was immersed in 4% paraformaldehyde, and formalin fixation was performed. Then, the tissue pieces were embedded by paraffin, and tissue pieces of the skin containing the mosaic cell aggregations were produced. The pieces were subjected to Hematoxylin-Eosin dye (HE dye).

Figure 2:
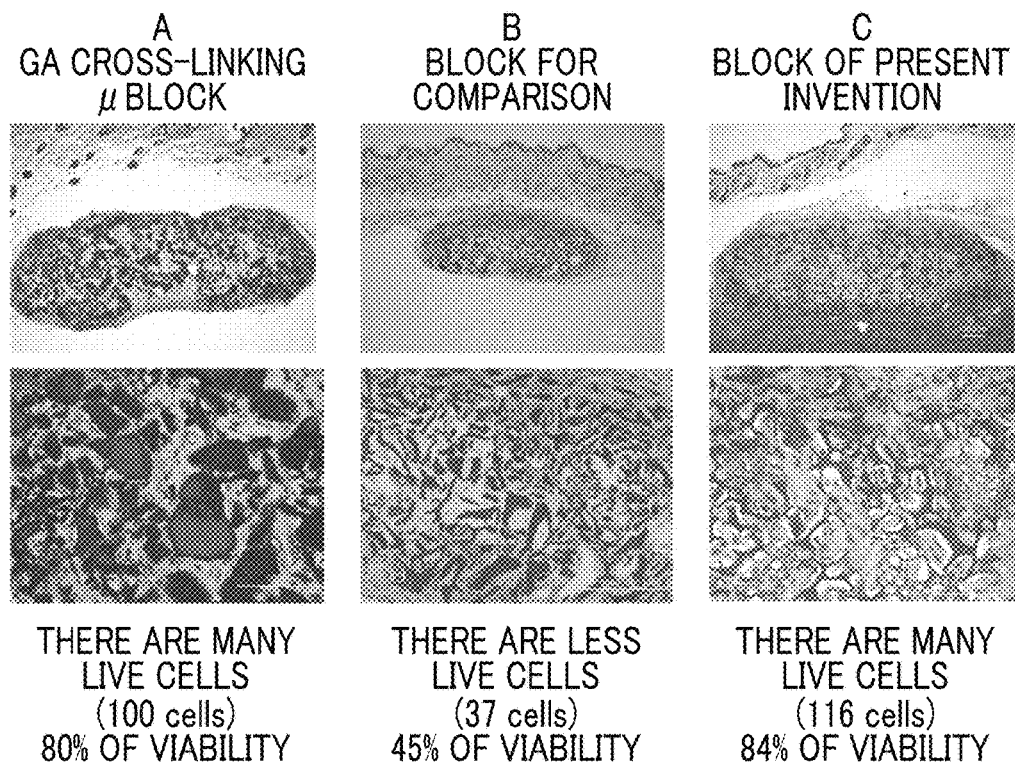
FIG. 2 shows difference (after 2 weeks) in a viable state of cells in hMSC mosaic cell aggregations in which a block used in the present invention or a block for comparison is used.

HE samples after 2 weeks of transplanting of a block of "7.5% being middle" in Example 10 and blocks in Comparative Examples 6 and 7 are shown in FIG. 2. The viability denoted in FIG. 2 indicates a proportion of the number of live cells in the number of all live cells (the number of live cells+the number of dead cells).

It can be seen that the number of live cells is small in a mosaic cell aggregation (B in FIG. 2: the number of live cells being 37: the viability being 45%) in which the block in Comparative Example 6 is used, compared to a mosaic cell aggregation (A in FIG. 2: the number of live cells being 100: the viability being 80%) in which the GA cross-linked µblock in Comparative Example 7 is used. In contrast, it was found that the number of live cells is large and the viability was satisfactory in a mosaic cell aggregation (C in FIG. 2: the number of live cells being 116: the viability being 84%) in which the block ("7.5% being middle) for the present invention in Example 10 was used, compared to the mosaic cell aggregation (B in FIG. 2: the number of live cells being 37: the viability being 45%) in which the block in Comparative Example 6 was used. It was found that these results are consistent with the results of the in vitro assay in Example 12, and it is possible to improve the viability of transplanted cells by employing the blocks for the present invention.

Figure 3:
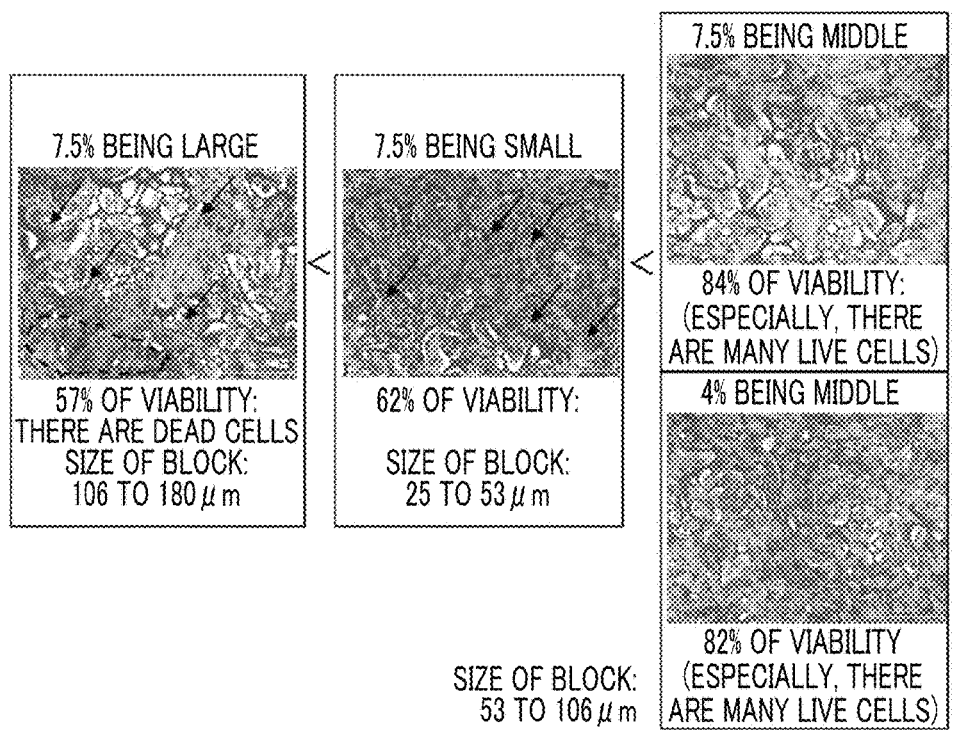
FIG. 3 shows a viable state of transplanted cells in a block group used in the present invention and shows existence of the cells in an hMSC mosaic cell aggregation and a difference of the viable state depending on the size of the blocks.

In addition, the viable state of transplanted cells in a block group for the present invention is shown in FIG. 3. The viability denoted in FIG. 3 indicates a proportion of the number of live cells in the number of all live cells (the number of live cells+the number of dead cells).

The viability of a block at "7.5% being large" having sizes of 106 to 180 µm was 57%, the viability of a block at "7.5% being small" was 62%, the viability of a block at "7.5% being middle" was 84%, and the viability of a block at "4% being middle" was 82%. That is, it was found that the viability of cells at "7.5% being small", "7.5% being middle", and "4% being middle" was more improved than that at "7.5% being large" having sizes of 106 to 180 µm in the block group for the present invention (FIG. 3). In addition, it was found that the viability of transplanted cells at "7.5 being middle" and "4% being middle" was more improved than that at "7.5 being small" as a viability bringing the best transplantation results (FIG. 3). That is, it was found that it was important that the present invention had a configuration such that the tap density of a macromolecular block or the value of "square root of cross-sectional area/peripheral length" in a two-dimensional cross-sectional image of a macromolecular block fell in a predetermined range, and in the range, the viability of cells after transplantation was sequentially improved in order of "53 to 106 µm">"25 to 53 µm">"106 to 180 µm".

Figure 4:
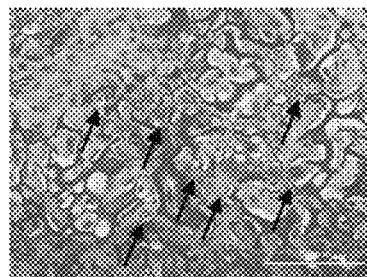
FIG. 4 shows angiogenesis in an hMSC mosaic cell aggregation 2 weeks after transplantation.

In addition, a HE sample after 2 weeks of transplantation in a case where the mosaic cell aggregation in Example 10 in which blocks for the present invention having sizes of 53 to 106 µm are used is transplanted is shown in FIG. 4. In addition, the number of blood vessels in FIG. 4 was measured, and the result was 63 pieces/mm$^2$. As shown in FIG. 4, it was also found that blood vessels are attracted to the inside of the mosaic cell aggregation.

Figure 5:
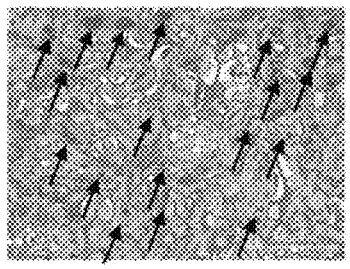
FIG. 5 shows angiogenesis in an hMSC+hECFC mosaic cell aggregation 2 weeks after transplantation.

Furthermore, a HE sample after 2 weeks of transplantation in a case where a mosaic cell aggregation into which vascular cells are put and representative blocks at "7.5% being middle" in Example 11 are used is transplanted is shown in FIG. 5. The number of blood vessels in FIG. 5 was measured, and the result was 180 pieces/mm$^2$. It became clear that more blood vessels were formed in the mosaic cell aggregation in the case where the mosaic cell aggregation in Example 11 into which vascular cells were put was transplanted as shown in FIG. 5, compared to the case of the transplantation of the mosaic cell aggregation in Example 10.

[Example 17] Calculation of Concentration and Proportion of ECFC in hMSC+hECFC Mosaic Cell Aggregation In a mosaic cell aggregation in which blocks at "7.5% being middle" representative in Example 9 were used, a piece was subjected to immunological dyeing using kits (for Universal K0673 of a Dako LSAB2 kit and for a dual rabbit•mouse primary antibody of Dako LSAB2 kit/HRP (DAB)) in which DAB color development was used in a CD31 antibody (EPT Anti CD31/PECAM-1) for hECFC dyeing. The proportion of the area of hECFC (vascular cells) in a center portion was obtained using image management software ImageJ (registered trademark) and through a dyeing method using a CD31 antibody. The "center portion" referred to herein is defined in the above.

As a result, the proportion of the area of hECFC (vascular cells) in the center portion of the mosaic cell aggregation at "7.5% being middle" representative in Example 9 was 99%.

Furthermore, in the mosaic cell aggregation at "7.5% being middle" representative in Example 9, the cell density of hECFC existing in the center portion was calculated by overlapping the above-described dye using a CD31 antibody with Hematoxylin-Eosin dye (HE dye). The density of vascular cells in the center portion can be obtained by actually counting the number of cells a sliced sample and dividing the number of cells by the volume. First, the number of cells was calculated by counting the number of cell nuclei of the HE dye overlapping the dye using CD31 antibody after overlapping the above-described two images using Photoshop. In contrast, the volume was obtained by obtaining the area of the center portion using ImageJ (registered trademark), and multiplying the area by 2 μm of the thickness of the sliced sample.

As a result, the number of cells of hECFC (vascular cells) in the center portion of the mosaic cell aggregation at "7.5% being middle" representative in Example 9 was $2.58 \times 10^4$ cells/m³.

[Example 18] Production of Porous Body (Macromolecular Porous Body) of Recombinant Peptide A cylindrical cup-shaped aluminum container with a thickness of 1 mm and a diameter of 47 mm was prepared. When the curved surface of the cylindrical cup is set as a side surface, the side surface of the container is closed by aluminum with 1 mm and the bottom surface (circular shape of a flat plate) is also closed by aluminum with 1 mm. In contrast, the upper surface is in an open shape. In addition, TEFLON (registered trademark) with a thickness of 1 mm is evenly spread over only the inside of the side surface, and as a result, the inner diameter of the cylindrical cup became 45 mm. Hereinafter, this container is referred to as a cylindrical container.

An aqueous recombinant peptide solution was prepared such that the final concentration of CBE3 was set to 7.5 mass %, and was made to flow into the cylindrical container. The aqueous recombinant peptide solution was cooled down from the bottom surface within a freezer using a cooling shelf. At this time, the process of cooling the liquid temperature was changed by changing the temperature of the cooling shelf, the thickness of a heat insulating plate (glass) which was interposed between the shelf and the cylindrical container, and the amount of aqueous recombinant peptide solution to be put. The temperature of the shelf at −40° C., −60° C., and −80° C., the glass with 0.7 mm, 1.1 mm, and 2.2 mm, and the amount of aqueous recombinant peptide solution being 4 mL, 12 mL, and 16 mL were combined.

In addition, since each of the aqueous solutions are cooled down from the bottom surface, it is most difficult for the temperature of the surface of water in the center portion of a circle to be cooled down. Accordingly, the portion thereof has the highest liquid temperature within the solution. Therefore, the liquid temperature of the portion thereof was measured (hereinafter, the liquid temperature in the above-described portion is referred to as the highest internal liquid temperature).

Figure 8:
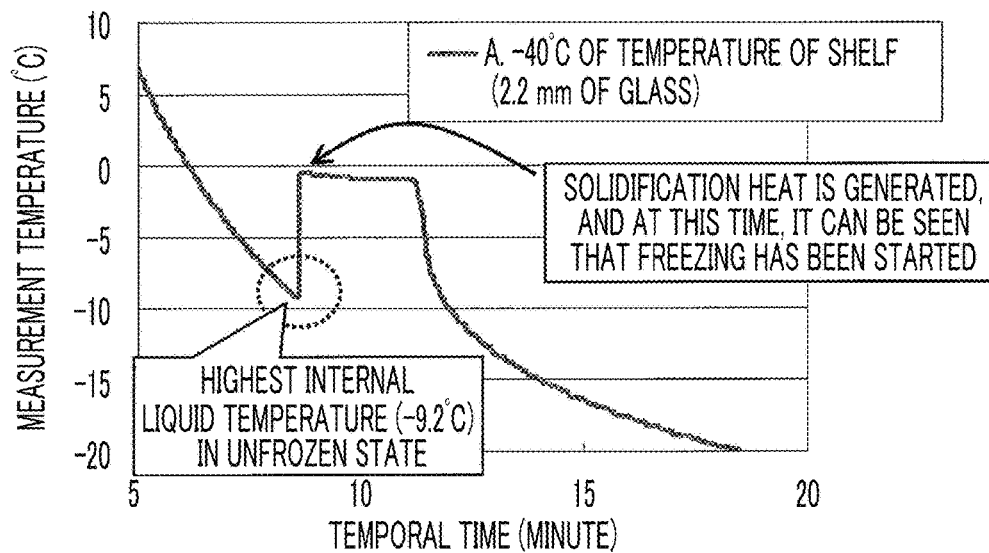
FIG. 8 shows a temporal change in the highest internal liquid temperature at −40° C. of the temperature of a shelf (2.2 mm of a glass).

As a result, the temperature does not start to increase until the highest internal liquid temperature becomes −9.2° C. in a case of the temperature of the shelf being −40° C. and the glass being 2.2 mm, and the solution enters a state (FIG. 8) in which the highest internal liquid temperature becomes lower than or equal to a "melting point of a solvent−3° C." in an unfrozen state. It was found that, after being kept in this state, the temperature started to increase at −9.2° C., and therefore, solidification heat was generated (FIG. 8). In addition, it was also possible to check that ice actually started to form at the timing. Thereafter, the temperature was kept at around 0° C. for a certain period of time. Here, the solution has entered a state in which a mixture of water and ice exists. The temperature started to decrease again from the last 0° C. At this time, the liquid portion had been disappeared and became ice (FIG. 8). The temperature being measured becomes a solid temperature within the ice, that is, not a liquid temperature. In this manner, whether or not the freezing was performed after the highest internal liquid temperature exceeds a "melting point of a solvent−3° C." in the unfrozen state can be found if the highest internal liquid temperature at the moment when solidification heat is generated is checked.

The highest internal liquid temperature in the unfrozen state at the moment when this solidification heat was generated was measured with respect to 6 kinds of the combination, and the results were as follows.

A: −9.2° C. in a case of the temperature of the shelf being −40° C., the glass with 2.2 mm, and the amount of liquid being 4 mL B: −8.3° C. in a case of the temperature of the shelf being −40° C., the glass with 1.1 mm, and the amount of liquid being 4 mL C: −2.2° C. in a case of the temperature of the shelf being −40° C., the glass with 0.7 mm, and the amount of liquid being 4 mL D: −7.2° C. in a case of the temperature of the shelf being −60° C., the glass with 2.2 mm, and the amount of liquid being 4 mL D referred to herein is the "condition b" referred to in Example 2.

E: −3.9° C. in a case of the temperature of the shelf being −80° C., the glass with 2.2 mm, and the amount of liquid being 4 mL F: −3.1° C. in a case of the temperature of the shelf being −80° C., the glass with 1.1 mm, and the amount of liquid being 4 mL G: 5.8° C. in a case of the temperature of the shelf being −80° C., the glass with 0.7 mm, and the amount of liquid being 4 mL H: −6.5° C. in a case of the temperature of the shelf being −40° C., the glass with 2.2 mm, and the amount of liquid being 12 mL I: −2.4° C. in a case of the temperature of the shelf being −40° C., the glass with 2.2 mm, and the amount of liquid being 16 mL Accordingly, A, B, D, E, F, and H are production methods performed through a freezing step in which the highest internal liquid temperature becomes a liquid temperature lower than or equal to a "melting point of a solvent−3° C." in an unfrozen state (frozen recombinant peptide blocks which satisfy highest internal liquid temperature "melting point of a solvent−3° C.").

In addition, C, G, and I are production methods performed through a freezing step in which the highest internal liquid temperature does not become a liquid temperature lower than or equal to a "melting point of a solvent−3° C." in an unfrozen state (frozen recombinant peptide blocks which satisfy highest internal liquid temperature>"melting point of a solvent−3° C.").

CBE3 porous bodies were obtained after freeze-drying the frozen recombinant peptide blocks which had been obtained in this manner. The origins of A, B, D, E, F, and H are called "CBE3 porous bodies which satisfy (highest internal liquid temperature "melting point of a solvent−3° C."), and the origins of C, G, and I are called "CBE3 porous bodies which satisfy (highest internal liquid temperature>"melting point of a solvent−3° C.").

Example 19

Evaluation of the hollow hole size and the hollow hole shape of a porous body was performed on the CBE3 porous bodies obtained in Example 18. After the obtained porous bodies were subjected to thermal cross-linking for 20 hours at 160° C. and were made insoluble, the porous bodies were swelled with a physiological salt solution for sufficient time. Thereafter, frozen tissue pieces were produced using a microtome, and Hematoxylin-Eosin (HE)) dyed samples were produced.

Figure 7A:
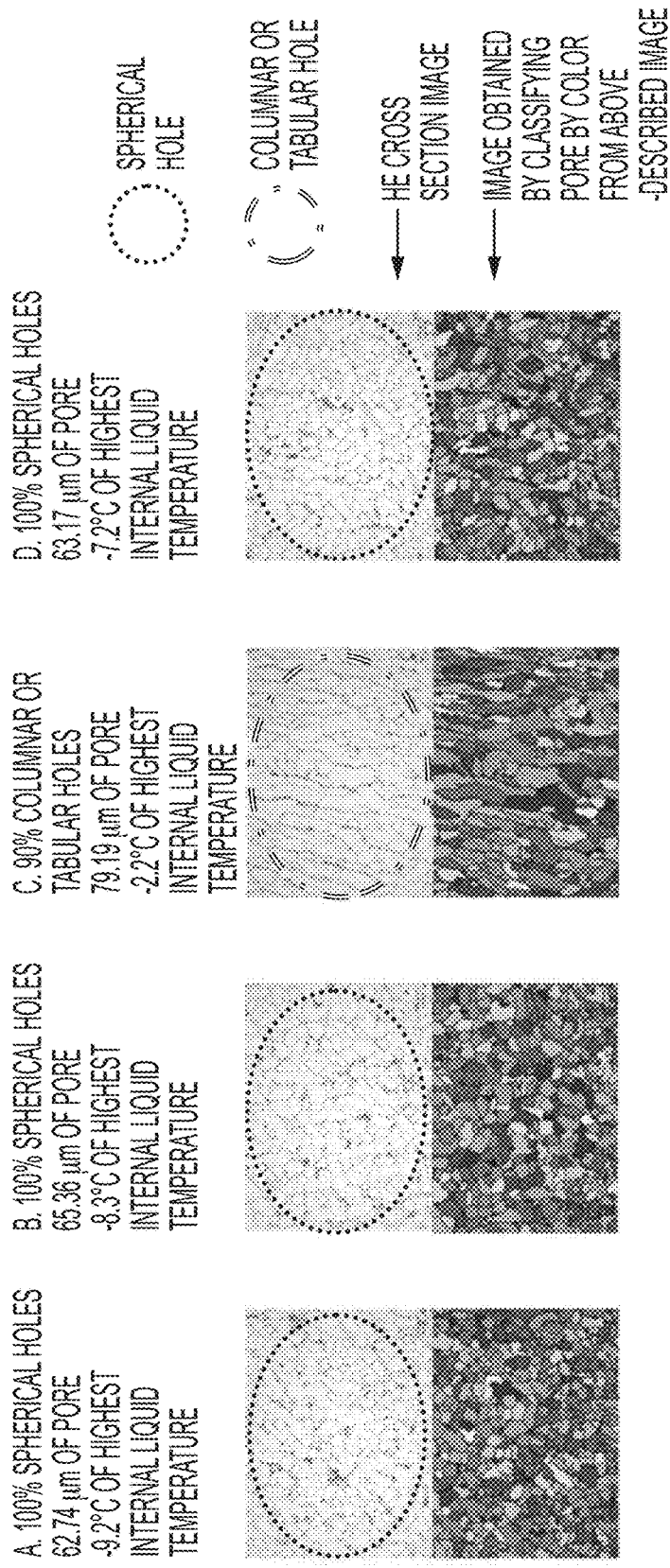
FIG. 7A and FIG. 7B shows a HE cross-sectional image and a pore shape of a CBE3 porous body, and a highest internal liquid temperature.
Figure 7B:
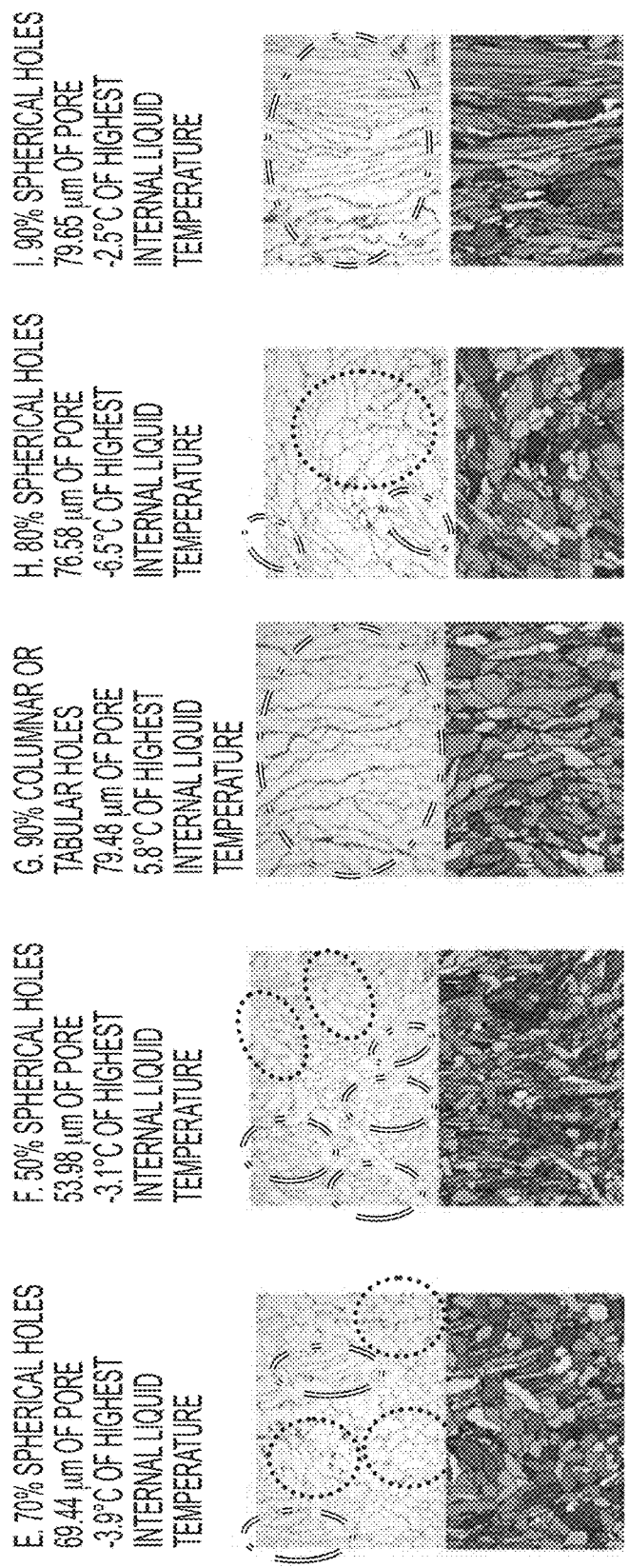

An image of a center portion of the obtained samples were shown in FIG. 7 (the highest internal liquid temperature>a "melting point of a solvent−3° C." and the highest internal liquid temperature≤a "melting point of a solvent−3° C."). As a result, in the cases of the highest internal liquid temperature>a "melting point of a solvent−3° C." (C, G, I), greater than or equal to 80% hollow holes became columnar or tabular holes, and spherical holes were less than or equal to 20%. In contrast, in the case of the highest internal liquid temperature≤a "melting point of a solvent−3° C." (A, B, D, E, F, H), greater than or equal to 50% of hollow holes became spherical holes. In addition, in the case of the highest internal liquid temperature≤a "melting point of a solvent−7° C." (A, B, D), almost all hollow holes were constituted of spherical holes since greater than or equal to 80% of hollow holes became spherical holes. Accordingly, it was found that it was important that the highest internal liquid temperature in an unfrozen state is lower than or equal to a "melting point of a solvent−3° C." in order to make the hollow holes of a porous body be holes having spherical shapes and it was possible to make almost all hollow holes be holes having spherical shapes by further making the highest internal liquid temperature be lower than or equal to a "melting point of a solvent−7° C.".

The shapes of hollow holes and the average pore sizes regarding A to I are as follows.
A: 100% spherical holes, 62.74 μm
B: 100% spherical holes, 65.36 μm
C: 90% columnar or tabular holes, 79.19 μm
D: 100% spherical holes, 63.17 μm
E: 70% spherical holes, 69.44 μm
F: 50% spherical holes, 53.98 μm
G: 90% columnar or tabular holes, 79.48 μm
H: 80% spherical holes, 76.58 μm
I: 90% columnar or tabular holes, 79.65 μm

[Example 20] Production of Recombinant Peptide Block (Grinding and Cross-Linking of Porous Body)

The CBE3 porous bodies obtained in Example 19 were ground using NEW POWERMILL (Osaka Chemical Co., Ltd., NEW POWERMILL PM-2005). The grinding was performed for one minute×5 times, that is, for 5 minutes in total at the maximum rotation speed. The obtained ground substance was divided according to the size using a stainless steel sieve to obtain recombinant peptide blocks at 25 to 53 μm and 53 to 106 μm. Thereafter, samples were obtained by performing thermal cross-linking for 72 hours at 160° C. under reduced pressure. These samples satisfied that the tap density was 10 mg/cm$^3$ to 500 mg/cm$^3$ or the value obtained by dividing a square root of a cross-sectional area of the above-described macromolecular block in a two-dimensional cross-sectional image by a peripheral length was 0.01 to 0.13. In mosaic cell aggregations produced using these samples in the same manner as in Examples 8 and 10, regarding the same in vitro assay as that in Example 12 and results of transplantation into animals using the same evaluation as that in Examples 14 to 16, all of the mosaic cell aggregations exhibited higher performance (higher viability of cells) than that of blocks for comparison, regardless of A to I. However, there was a slight difference in performance when the difference in performance in A to I was checked. The order of the performance was that A, B, and D had the highest performance, E, F, and H had the next highest performance, and then, C, G, and I had the next highest performance. That is, this shows that there is a difference in performance depending on the shapes of hollow holes of a porous body. In Example 16, D (the "condition b" referred to in Example 2) has been described in detail as a representative result.

[Example 21] for Treatment of Cerebral Infarction: Freezing Step of Macromolecular Solution and Drying Step A cylindrical cup-shaped polytetrafluoroethylene (PTFE) container with a bottom surface thickness of 3 mm, a diameter of 51 mm, a side surface thickness of 8 mm, and a height of 25 mm was prepared. When the curved surface of the cylindrical cup is set as a side surface, the side surface of the cup is closed by PTFE with 8 mm and the bottom surface (circular shape of a flat plate) is also closed by PTFE with 3 mm. In contrast, the upper surface is in an open shape. Accordingly, the inner diameter of the cylindrical cup is set to 43 mm. Hereinafter, this container is referred to as a PTFE thickness • cylindrical container.

An aqueous CBE3 solution was made to flow into a PTFE thickness • cylindrical container and was cooled down from the bottom surface within a vacuum freeze dryer (TF5-85ATNNN: Takara Co., Ltd.) using a cooling shelf. A combination of settings for the container, the final concentration of the aqueous CBE3 solution, the liquid amount, and the temperature of the shelf at that time was prepared as described below.

The PTFE thickness • cylindrical container was used, the final concentration of the aqueous CBE3 solution was 4 mass %, and the amount of the aqueous solution was 8 mL.

As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. Accordingly, a porous body was obtained.

[Example 22] for Treatment of Cerebral Infarction: Measurement of Highest Internal Liquid Temperature in Unfrozen State in Each Freezing Step The highest internal liquid temperature in an unfrozen state in the solution in Example 21 was measured in the same manner as in Example 18. As a result, the liquid temperature was below 0° C. which was a melting point in a setting section of −10° C. of the temperature of the shelf (before the temperature was decreased to −20° C.), and the solution entered (unfrozen and supercooled) states in which freezing had not been caused in the state. Thereafter, a timing at which the liquid temperature was steeply increased to around 0° C. by further decreasing the temperature of the shelf to −20° C. was checked. Here, it was found that solidification heat was generated and freezing was started. In addition, it was also possible to check that ice actually started to form at the timing. Thereafter, the temperature was kept at around 0° C. for a certain period of time. Here, the solution has entered a state in which a mixture of water and ice exists. The temperature started to decrease again from the last 0° C. At this time, the liquid portion had been disappeared and became ice. Accordingly, the temperature being measured became a solid temperature within the ice, that is, not the liquid temperature (refer to FIG. 9).

As can be seen from FIG. 9, the highest internal liquid temperature was −8.8° C. Accordingly, it was found that the highest internal liquid temperature was lower than or equal to a "melting point of a solvent−3° C.".

In contrast, the temperature difference between a liquid temperature of a cooled surface and the highest internal liquid temperature (a liquid temperature of a non-cooled surface) in a case where the temperature at a position closest to a cooling side is defined as the liquid temperature of a cooled surface and is measured, with respect to the highest internal liquid temperature (the liquid temperature of the non-cooled surface) in the vicinity of the surface of water is denoted below.

The temperature difference when the liquid temperature of a non-cooled surface is set to a melting point (0° C.), the temperature difference immediately before the temperature of a shelf is decreased to −20° C. from −10° C., and the temperature difference immediately before generation of solidification heat are denoted. The expression "temperature difference immediately before" indicates the highest temperature in the difference in the temperature which can be detected between a period of 1 second before the above-described event and 20 seconds before the above-described event.

Highest internal liquid temperature (liquid temperature of non-cooled surface) in unfrozen state immediately before generation of solidification heat: −8.8° C.
Temperature difference when liquid temperature of non-cooled surface becomes melting point (0° C.): 1.1° C.
Temperature difference immediately before temperature is decreased to −20° C. from −10° C.: 0.2° C.
Temperature difference immediately before generation of solidification heat: 1.1° C. (Refer to FIG. 9)

[Example 23] for Treatment of Cerebral Infarction: Production of Macromolecular Block (CBE3 Block) from CBE3 Porous Body (Grinding and Cross-Linking of Porous Body)

The CBE3 porous bodies obtained in Example 21 were ground using NEW POWERMILL (Osaka Chemical Co., Ltd., NEW POWERMILL PM-2005). The grinding was performed for one minute×5 times, that is, for 5 minutes in total at the maximum rotation speed. The obtained ground substance was divided according to the size using a stainless steel sieve to obtain uncross-linked blocks at 25 to 53 μm, 53 to 106 μm, and 106 μm to 180 μm. Thereafter, samples of CBE3 blocks were obtained by performing thermal cross-linking (the cross-linking was performed for 6 kinds of cross-linking time including 8 hours, 16 hours, 24 hours, 48 hours, 72 hours, and 96 hours) at 160° C. under reduced pressure. Hereinafter, cross-linking was performed for 48 hours. The difference in cross-linking time does not affect the performance in the evaluation of this application. Therefore, here, blocks which have been cross-linked for 48 hours are representatively used.

[Example 24] for Treatment of Cerebral Infarction: Tap Density of CBE3 Block

The tap density of a CBE3 block (53 to 106 μm) which had been produced in Example 23 was measured in the same manner as in Example 6. As a result, the CBE3 block in Example 23 had a tap density of 135 mg/cm$^3$. Accordingly, it was found that the CBE3 block in Example 23 satisfied the range of the tap density being 10 mg/cm$^3$ to 500 mg/cm$^3$ referred to in Examples 12 and 20.

[Example 25] for Treatment of Cerebral Infarction: Calculation of "Square Root of Cross-Sectional Area/Peripheral Length" in Two-Dimensional Cross-Sectional Image of CBE3 Block A value of a "square root of cross-sectional area/peripheral length" of the CBE3 block (53 to 106 μm) which had been produced in Example 23 was measured in the same manner as in Example 7. As a result, the block in Example 23 had a value of 0.053. Accordingly, it was found that the CBE3 block in Example 23 satisfied the range of the value obtained by dividing a square root of a cross-sectional area by a peripheral length being 0.01 to 0.13 referred to in Examples 12 and 20.

[Example 26] Production of Mosaic Cell Aggregation (GFP Expression Rat MSC) in which CBE3 Block is Used Green fluorescent protein (GFP) expression rat bone marrow-derived mesenchymal stem cells (GFP rat MSC: Fischer 344 (F344) Rat mesenchymal Stem Cells with GFP, CSC-C1313, Creative Bioarray) were adjusted to 100000 cells/mL using a recommended proliferation medium, and CBE3 blocks (53 to 106 μm) which had been produced in Example 23 were added thereto so as to make a concentration of 0.1 mg/mL. 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the CBE3 blocks and hMSC cells and was in a spherical shape with a diameter of about 1 mm, was produced. Since the mosaic cell aggregation was produced in a U-shaped plate, this mosaic cell aggregation was in a spherical shape (referred to as a GFP expression rat MSC mosaic cell aggregation). Regarding all of the same in vitro assay as that in Example 12 and results of transplantation into animals using the same evaluation as that in Examples 14 to 16, this mosaic cell aggregation exhibited high performance (higher viability of cells) which was almost the same as that of the mosaic cell aggregation in which D in Example 20 was used.

[Example 27] Production of Mosaic Cell Aggregation (SD Rat Bone Marrow Cell) in which CBE3 Block is Used Sprague-Dawley (SD) rat bone marrow cells (rat BMSC, BMC01, COSMO BIO co., ltd.) were adjusted to 150000 cells/mL using a recommended proliferation medium (COSMO BIO co., ltd.: culture medium for bone marrow cell, BMCM), and the CBE3 blocks (53 to 106 μm) which had been produced in Example 23 was added thereto so as to make a concentration of 0.15 mg/mL. 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the CBE3 blocks and hMSC cells and was in a spherical shape with a diameter of about 1 mm, was produced. Since the mosaic cell aggregation was produced in a U-shaped plate, this mosaic cell aggregation was in a spherical shape. Regarding all of the same in vitro assay as that in Example 12 and results of transplantation into animals using the same evaluation as that in Examples 14 to 16, this mosaic cell aggregation exhibited high performance (higher viability of cells) which was almost the same as that of the mosaic cell aggregation in which D in Example 20 was used.

[Example 28] Production of Mosaic Cell Aggregation (hMSC) in which CBE3 Block is Used Human bone marrow-derived mesenchymal stem cells (hMSC) were adjusted to be 100000 cells/mL using a proliferation medium (TAKARA BIO INC.: MSCGM BulletKit (registered trademark)), and CBE3 blocks (53 to 106 μm) which had been produced in Example 23 were added thereto so as to make a concentration of 0.1 mg/mL. 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation (0.001 μg of blocks per cell), which was formed of the CBE3 blocks and hMSC cells and was in a spherical shape with a diameter of about 1 mm, was produced. Since the mosaic cell aggregation was produced in a U-shaped plate, this mosaic cell aggregation was in a spherical shape. Regarding all of the same in vitro assay as that in Example 12 and results of transplantation into animals using the same evaluation as that in Examples 14 to 16, this mosaic cell aggregation exhibited high performance (higher viability of cells) which was almost the same as that of the mosaic cell aggregation in which D in Example 20 was used.

[Comparative Example 8] Cell-Containing CBE3 Sponge

The CBE3 porous body obtained in Example 21 was molded in φ5 mm×1 mm to obtain CBE3 sponge. $1.2 \times 10^4$ cells/piece were sown in this CBE3 sponge in a state where GFP expression rat bone marrow-derived mesenchymal stem cells (GFP rat MSC: Fischer 344 (F344) Rat mesenchymal Stem Cells with GFP, CSC-C1313, Creative Bioarray) were suspended in a recommended medium to proliferate cells up to $0.5 \times 10^6$ cells/piece by performing culturing for 24 days. Accordingly, cell-containing CBE3 sponge was obtained.

[Example 29] Production of Animal Model of Rat with Cerebral Infarction (MCAO Model SD Rat)

The right brain with cerebral infarction was prepared by performing middle cerebral artery occlusion (MCAO) on a male SD rat at the age of 9 weeks similarly to a method disclosed in "Neurosurgery 68(6): 1733 to 1742, June 2011, T Sugiyama et al. Therapeutic Impact of Human Bone Marrow Stromal Cells Expanded by Animal Serum-Free Medium for Cerebral Infarct in Rats". The right temporal region of the rat and the cranial bone were opened under isoflurane anesthesia. The middle cerebral artery was ligated with a suture bone. Blood vessels within a field of view were cauterized using a bipolar coagulator to close the head. Thereafter, a cerebral infarction model was produced by temporarily ligating the carotid artery for 90 minutes and resuming the blood flow.

A motor function evaluation was performed through Rotarod or through quantifying improvement of an action of turning left. In the evaluation of Rotarod, acceleration at 4 to 40 rpm for 300 seconds was set and 6 tests per day were performed at an interval of 5 minutes or longer for each test. The average value of these 6 tests was evaluated as a proportion (%) (normally being 100%) with respect to a normal numerical value of the same animal.

In addition, the action of turning left is based on an observation of deterioration in a function of the left side of the body due to cerebral infarction caused in the right brain in this MCAO model. Specifically, an evaluation on which direction the rat first faced to in a state in which only front two legs of the rat were put on the ground and rear two legs of the rat were floating in the air was performed. The direction was evaluated as −1 point for the left, 0 points for the straight, and 0 points for the right by digitalizing the average value, which had been obtained by performing 6 tests. A normal rat gets 0 points since it proceeds straight, and a rat with right cerebral infarction gets a value close to −1 point since it moves counterclockwise.

[Example 30] Production of Animal Model of Rat with Cerebral Infarction (MCAO Model SD Rat)

The right brain with cerebral infarction on which middle cerebral artery occlusion (MCAO) was performed on an immunodeficient nude male rat at the age of 9 weeks was prepared in the same manner as in Example 29. As the evaluation of a motor function of this, an evaluation of an action of turning left was also performed through the same method as that in Example 29.

[Example 31] Administration of Mosaic Cell Aggregation of GFP Expression Rat MSC, Cell Suspension, or Cell-Containing CBE3 Sponge to Rat with Cerebral Infarction GFP expression rat MSC mosaic cell aggregation produced in Example 26, a cell suspension in a state, in which the same cells were suspended in 100 μL of PBS and which was used as a comparative example, or cell-containing CBE3 sponge produced in Comparative Example 8 was administered to the MCAO model SD rat produced in Example 29 as local administration after 7 days of the onset (MCAO treatment), by performing direct transplantation into the vicinity of the area with cerebral damage.

The administered amount was comparatively evaluated in a state in which the numbers of cells administered in the administration groups were combined after setting the number of GFP expression rat MSC mosaic cell aggregations to 25 pieces/rat (the number of cells being $0.5 \times 10^6$ cells/rat=$1.34 \times 10^6$ cells/kg body weight), the cell suspension to $0.5 \times 10^6$ cells/rat, and the number of pieces of cell-containing CBE3 sponge to 1 piece/rat (the number of cells being $0.5 \times 10^6$ cells/rat). The number of animals was set to 10 animals in each group.

[Example 32] Improvement in Motor Function of Rat with Cerebral Infarction (GFP Expression Rat MSC Mosaic Cell Aggregation)

Figure 10:
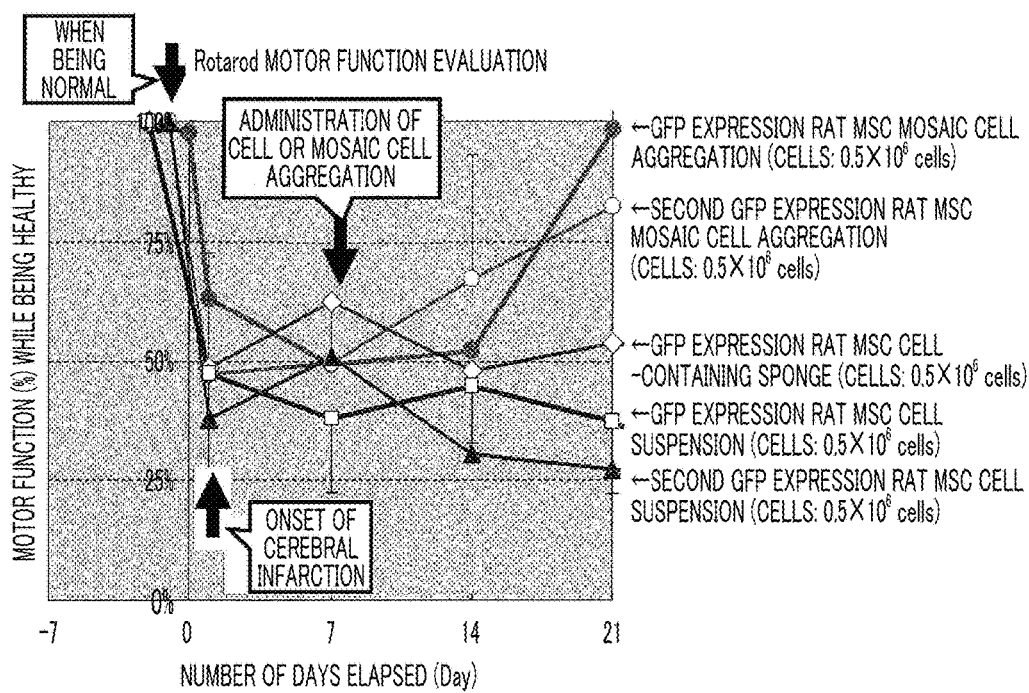
FIG. 10 shows an improvement of a motor function due to administration of a GFP expression rat MSC mosaic cell aggregation to a rat with cerebral infarction.

As a result of Example 31, as shown in FIG. 10, it was found that extremely remarkable improvement in a motor function was recognized on days 14 and 21 after the administration (administration on day 7 in the graph) in the mosaic cell aggregations in a state in which GFP expression rat MSC was used as cells. In contrast, there was no improvement in the motor function in the administration of the cell suspension used for comparison, even after the administration. Similarly, there was no remarkable effect also in the cell-containing CBE3 sponge for comparison, unlike in the mosaic cell aggregations, and the motor function was leveled off as it was. The same test was performed twice with respect to the administration of the mosaic cell aggregations and the cell suspension, and therefore, the "second" data was shown in the graph.

Accordingly, it was found that the degree of the effect of improvement in the motor function was the "mosaic cell aggregations">>the "cell-containing sponge" the "cell suspension". In addition, it was found that it was possible to obtain the effect even if the mosaic cell aggregations were used in an acute phase such as day 7 after the generation of infarction. This means that it is possible to obtain the effect even at a timing which is not an ultra acute phase within 48 hours. Furthermore, GFP expression rat MSC used for the transplantation was Fischer rat cells and the rat with cerebral infarction to which the GFP expression rat MSC was administered was a SD rat. Therefore, it was found that it was possible to obtain an effect of treating cerebral infarction even in the same kinds of cells from another rat.

[Example 33] Administration of Mosaic Cell Aggregation of SD Rat Bone Marrow Cell, or Cell Suspension to Rat with Cerebral Infarction Mosaic cell aggregations of SD rat bone marrow cells produced in Example 27, or a cell suspension in a state, in which the same cells were suspended in 100 µL of PBS and which was used as a comparative example was administered to the MCAO model SD rat produced in Example 29 as local administration after 7 days of the onset (MCAO treatment), by directly performing injection into the vicinity of the area with cerebral damage using a syringe.

The administered amount was comparatively evaluated in which the number of cells was changed, in a state where the numbers of cells administered in the administration groups were combined after setting the number of mosaic cell aggregations of SD rat bone marrow cells to 53 pieces/rat and 13 pieces/rat (the number of cells being $1.6 \times 10^6$ cells/rat=$4.35 \times 10^6$ cells/kg body weight, $0.38 \times 10^6$ cells/rat=$1.33 \times 10^6$ cells/kg body weight) and the cell suspension to $1.6 \times 10^6$ cells/rat and $0.38 \times 10^6$ cells/rat. The number of animals was set to 10 animals in each group.

[Example 34] Improvement in Motor Function of Rat with Cerebral Infarction (Mosaic Cell Aggregation of SD Rat Bone Marrow Cell)

Figure 11:
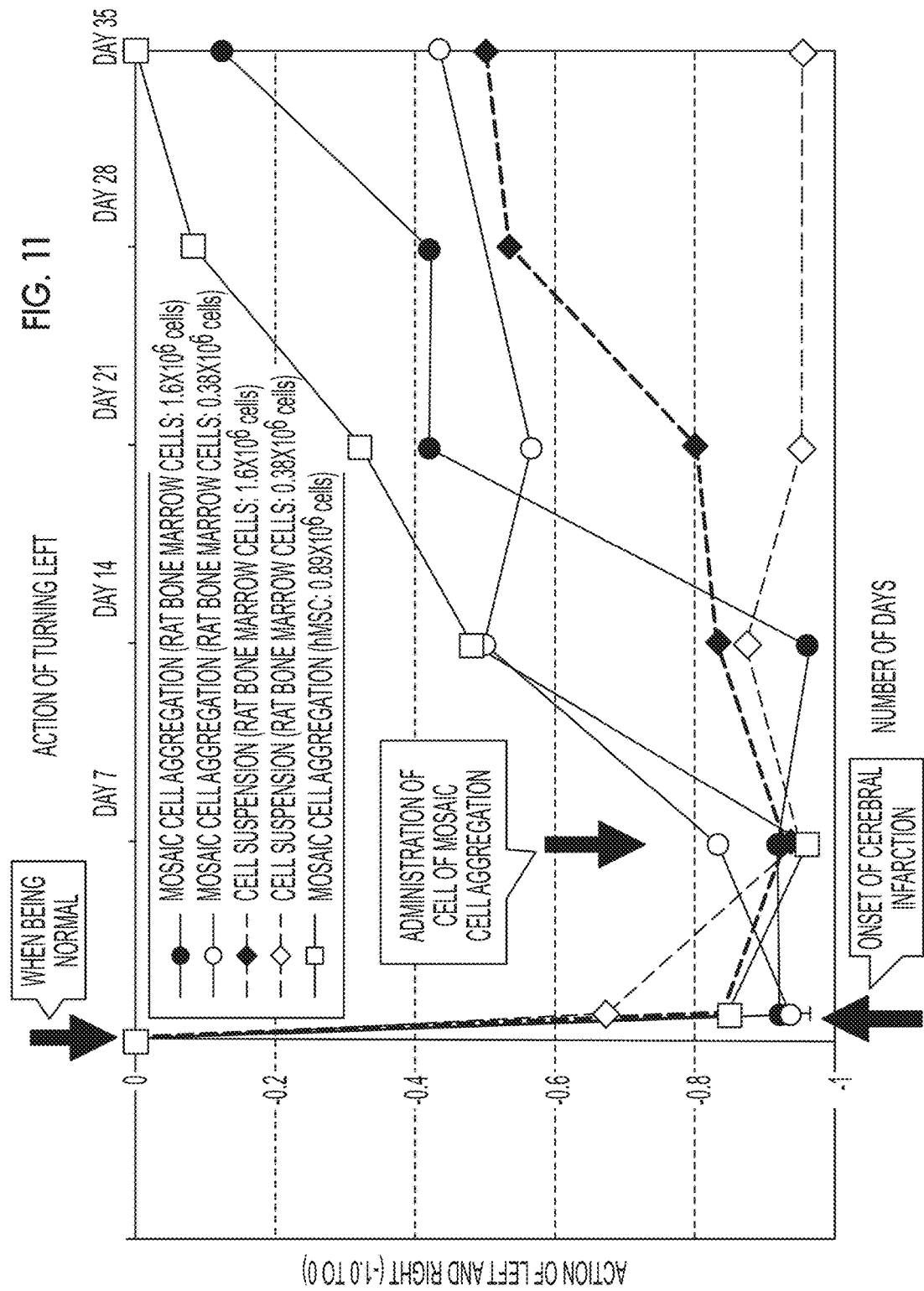
FIG. 11 shows an improvement of a motor function due to administration of mosaic cell aggregations of rat bone marrow cells to rats with cerebral infarction and administration of hMSC mosaic cell aggregation to a cerebral infarction-developed nude rat.

As a result of Example 33, as shown in FIG. 11, it was found that extremely remarkable improvement in a motor function of the action of turning left was recognized on days 21, 28, and 35 after the administration (administration on day 7 in the graph) in the mosaic cell aggregations in a state in which SD rat bone marrow cells were used as cells. In addition, the effect of the improvement was high in the mosaic cell aggregations in which the number of cells was large. In contrast, there was no improvement in the motor function in the administration of the cell suspension used for comparison in the group with a small number of cells ($0.38 \times 10^6$ cells/rat). In addition, even if a large number of cells ($1.6 \times 10^6$ cells/rat) was administered, the improvement in the motor function is limited in the cell suspension group. Accordingly, it became clear that, as a matter of course, the improvement was remarkably low compared to the group to which the same number of mosaic cell aggregations was administered, and the improvement in the motor function was more deteriorated compared to the mosaic cell aggregation group with a small number of cells.

To summarize these results, the degree of the effect of improvement in the motor function was the "mosaic cell aggregations with a large number of cells ($1.6 \times 10^6$ cells/rat)">the "mosaic cell aggregations with a small number of cells ($0.38 \times 10^6$ cells/rat)">the "cell suspension with a large number of cells ($1.6 \times 10^6$ cells/rat)">>the "cell suspension with a small number of cells ($0.38 \times 10^6$ cells/rat)".

[Example 35] Administration of Mosaic Cell Aggregation of hMSC to Rat with Cerebral Infarction and Immunodeficiency The hMSC mosaic cell aggregations produced in Example 28 was administered to the MCAO model SD rat (with immunodeficiency) produced in Example 30 as local administration after 7 days of the onset (MCAO treatment), by performing direct transplantation into the vicinity of the area with cerebral damage. As the administered amount, the number of hMSC mosaic cell aggregations was set to 45 pieces/rat (the number of cells being $0.89 \times 10^6$ cells/rat=$5.50 \times 10^6$ cells/kg body weight). The number of animals was set to 10 animals in each group.

[Example 36] Improvement in Motor Function of Rat with Cerebral Infarction (hMSC Mosaic Cell Aggregation)

As a result of Example 35, as shown in FIG. 11, it was found that extremely remarkable improvement in a motor function of the action of turning left was recognized on days 14, 21, 28, and 35 after the administration (administration on day 7 in the graph) in the mosaic cell aggregations in a state in which hMSC was used as cells.

Accordingly, it became clear that it was possible to check the effect in a state in which human cells were used. At the same time, from the facts that the cells used for the transplantation were human cells and a side into which the cells were transplanted was the rat. It was found that it was possible to obtain the effect of treating cerebral infarction also using heterologous cells in the immunodeficiency state.

[Example 37] Analysis of Expression of hMSC

Expression of a nervous system gene regarding hMSC used in Example 28 was analyzed. An RT-PCR technique was used for the analysis. A primer was purchased from TaqMan (registered trademark) Gene Expression Assays of life technologies applied biosystems. The subjects which have been analyzed are Sox2 (Cat.#4331182 Hs01053049_Amplicon Lenghe: 91), Nestin (Nestin, Cat.#4331182 Hs04187831_g1 Amplicon Lenghe: 58), NeuroD1 (Neurogenic differentiation 1, Cat.#4331182 Hs01922995_s1 Amplicon Lenghe: 110), GAD1 (GABA synthesis, Cat.#4331182 Hs01065893_m1 Amplicon Lenghe: 100), GRIA1 (glutamic acid receptor 1, Cat.#4331182 Hs00181348_s1 Amplicon Lenghe: 86), GRIA2 (glutamic acid 2, Cat.#4331182 Hs00181331_m1 Amplicon Lenghe: 71), CHRM1 (acetylcholine receptor 1, Cat.#4331182 Hs00265195_s1 Amplicon Lenghe: 82), GABRA1 (GABAA receptor α1, Cat.#4331182 Hs00971228_m1 Amplicon Lenghe: 82), GABBR1 (GABAB receptor 1, Cat #4331182 Hs00559488_m1 Amplicon Lenghe: 68), CHAT (acetylcholine synthesis, Cat.#4331182 Hs00252848_m1 Amplicon Lenghe: 64), DDC (serotonin/DOPA synthesis, Cat.#4351372 Hs01105048_m1 Amplicon Lenghe: 70), HTR1A (serotonin receptor 1A, Cat.#4331182 Hs00265014_s1 Amplicon Lenghe: 75), HTR1B (serotonin receptor 1B, Cat.#4331182 Hs00265286_s1 Amplicon Lenghe: 67), HTR2A (serotonin receptor 2A, Cat.#4331182 Hs01033524_m1 Amplicon Lenghe: 99), 5-HTT (serotonin transporter, Cat.#4331182 Hs00984349_m1 Amplicon Lenghe: 58), Ascl1 (neural stem cell neuronal differentiation marker, Cat.#4351372 Hs04187546_g1 Amplicon Lenghe: 81), Hes1 (neural stem cell astrocyte differentiation marker, Cat.#4331182 Hs00172878_m1 Amplicon Lenghe: 78), and Olig2 (neural stem cell oligodendrocyte differentiation marker, Cat.#4331182 Hs00300164_s1 Amplicon Lenghe: 86).

In order to find the relation of the expression amount, the magnitude relation of the expression was checked by performing RT-PCR at a normal concentration (RT-PCR was performed using 200 ng extraction RNA) and RT-PCR at a high concentration (RT-PCR was performed using 1000 ng extraction RNA).

RT-PCR was Performed Under the Following Conditions.

RNA extraction from cells were performed through a protocol using an extraction kit NucleoSpin RNA XS (#U0902A of MACHEREY-NAGEL GmbH & Co. KG). As a reagent kit of RT-PCR, PrimeScript One Step RT-PCR Kit ver.2 (Dye Plus) (TaKaRa PR057A) was used. As the conditions of a thermal cycler of RT-PCR, the processing was performed for 30 minutes at 50° C. and for 2 minutes at 94° C. Then, "30 seconds at 94° C., 30 seconds at 60° C., and 15 seconds at 72° C." was set as a cycle, and 50 cycles were performed.

The results are as summarized in Table 1. The symbols in the table means as follows.

++: In a case where it was possible to detect a target gene in all of general PCR and PCR with high concentration.

+: In a case where it was impossible to supplement in general PCR, but it was possible to detect a target gene in PCR with high concentration.

−: In a case where it was impossible to detect a target gene in both general PCR and PCR at a high concentration.

As to whether it was possible to detect the target gene was determined based on whether it was possible to visually check a band through electrophoresis.

TABLE 1

|  | sox2 | Nestin | NeuroD1 | GAD1 | GRIA1 | GRIA2 | CHRM1 | GABRA1 | GABBR1 |
|---|---|---|---|---|---|---|---|---|---|
| Expression in hMSC | ++ | ++ | + | ++ | ++ | ++ | − | ++ | + |

|  | CHAT | DDC | HTR1A | HTR1B | HTR2A | 5-HTT | Ascl1 | Hes1 | Olig2 |
|---|---|---|---|---|---|---|---|---|---|
| Expression in hMSC | − | + | − | + | ++ | + | − | ++ | − |

Example 38

Figure 12:
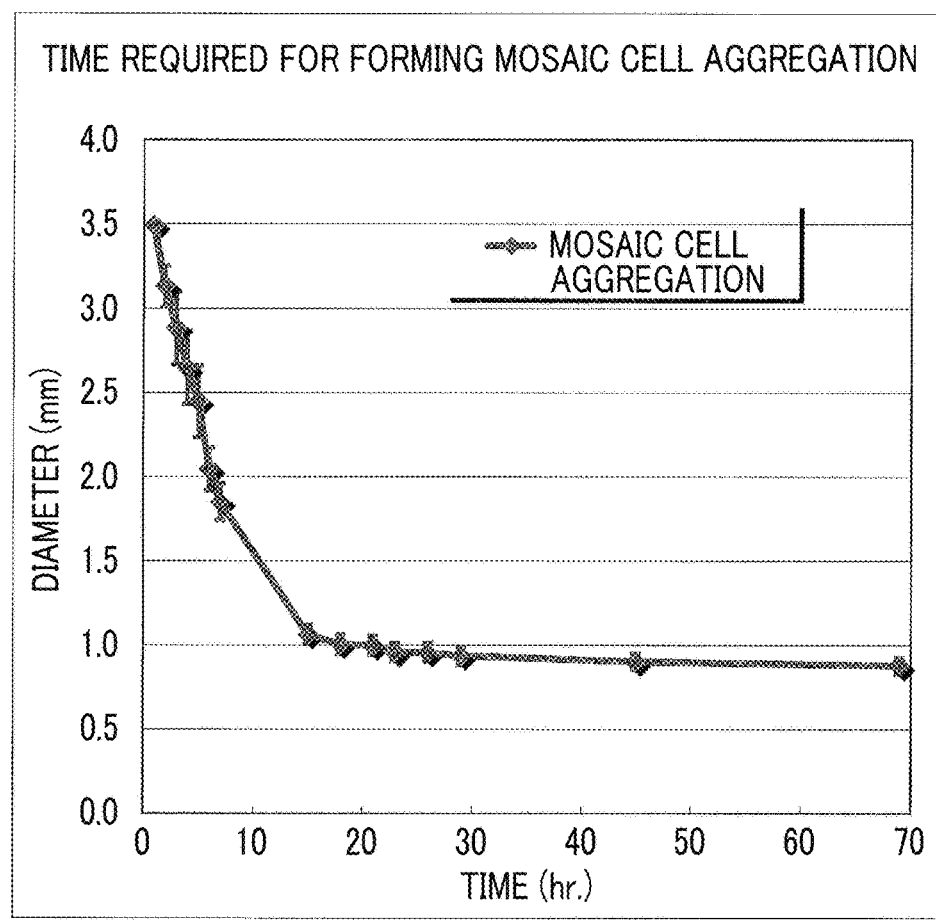
FIG. 12 shows a result in which the time required for forming a mosaic cell aggregation is checked.

In Examples 26, 27, and 28, the mosaic cell aggregations were formed by allowing the CBE3 blocks and the cells to stand for 24 hours. In Example 38, the required time for forming the mosaic cell aggregations was checked under the same conditions as those in Example 28 using the same CBE3 blocks and the same cells as in Example 28. The process in which the cell structures (mosaic cell aggregations) were formed was checked with a microscope using a U-shaped plate. At the beginning, the CBE3 blocks and the cells are dispersed. A result obtained by measuring the length of the spread of the dispersion is shown in FIG. 12. The diameter on a longitudinal axis in FIG. 12 indicates the length of the spread of the blocks and the cells. The length (diameter) of the spread of the blocks and the cells is decreased as the cell structures are formed. As can be seen from the result in FIG. 12, the mosaic cell aggregations referred to in the present invention were not generated in states in which the CBE3 blocks and the cells are allowed to stand for 1 hour, 2 hours, 3 hours, 4 hours, 5 hours, 6 hours, and 7 hours after being mixed and exist in a separate state. That is, in FIG. 12, it can be seen that the aggregations are not gathered to one aggregation since the length of the spread of the blocks and the cells is decreased in states in which the blocks and the cells are allowed to stand for 1 hour, 2 hours, 3 hours, 4 hours, 5 hours, 6 hours, and 7 hours. In contrast, it can be seen that the formation of one mosaic cell aggregation has been completed since the length (diameter) of the spread of the blocks and the cells is not changed in states in which the blocks and the cells are allowed to stand for 15 hours, 18 hours, 21 hours, 23 hours, 26 hours, 29 hours, 45 hours, and 69 hours.

What is claimed is:

1. A cell structure for brain damage treatment which contains biocompatible macromolecular blocks and at least one kind of cell and in which a plurality of the biocompatible macromolecular blocks are disposed in gaps between a plurality of the cells,
wherein the tap density of the biocompatible macromolecular block is 10 mg/cm$^3$ to 500 mg/cm$^3$ or a value obtained by dividing a square root of a cross-sectional area in a two-dimensional cross-sectional image of the biocompatible macromolecular block by a peripheral length is 0.01 to 0.13,
wherein the biocompatible macromolecular block is a biocompatible macromolecular block produced through a method including
a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and
a step (b) of freeze-drying the frozen biocompatible macromolecules which have been obtained in the step (a).

2. The cell structure for brain damage treatment according to claim 1,
wherein the cells include at least mesenchymal stem cells and/or bone marrow cells.

3. The cell structure for brain damage treatment according to claim 1,
wherein the number of cells, to be administered, per administration is 1.0×10$^5$ to 1.0×10$^7$ pieces/kg body weight.

4. The cell structure for brain damage treatment according to claim 1,
wherein the brain damage includes brain injury, hypoxic-ischemic brain damage, cerebral infarction, and/or cerebral stroke.

5. The cell structure for brain damage treatment according to claim 1,
wherein the size of one of the biocompatible macromolecular blocks is 10 μm to 300 μm.

6. The cell structure for brain damage treatment according to claim 1,
wherein the thickness or the diameter of the cell structure is 400 μm to 3 cm.

7. The cell structure for brain damage treatment according to claim 1,
wherein the cell structure includes 0.0000001 μg to 1 μg of a biocompatible macromolecular block per cell.

8. The cell structure for brain damage treatment according to claim 1,
wherein the biocompatible macromolecular block consists of a recombinant peptide.

9. The cell structure for brain damage treatment according to claim 8,
wherein the recombinant peptide is any of
a peptide formed of an amino acid sequence described in SEQ ID No: 1,
a peptide formed of an amino acid sequence in which one or a plurality of amino acids are deleted, substituted, or added in the amino acid sequence described in SEQ ID No: 1, and has biocompatibility, or
a peptide formed of an amino acid sequence having 80% or more sequence identity to the amino acid sequence described in SEQ ID No: 1, and has biocompatibility.

10. The cell structure for brain damage treatment according to claim 1,
wherein, in the biocompatible macromolecular block, the biocompatible macromolecules are cross-linked using heat, ultraviolet rays, or enzymes.

11. The cell structure for brain damage treatment according to claim 1,
wherein the biocompatible macromolecular block is in a granule form obtained by grinding a porous body of a biocompatible macromolecule.

12. The cell structure for brain damage treatment according to claim 1,
wherein the method of producing further comprises a step (c) of grinding a porous body which has been obtained in the step (b).

13. The cell structure for brain damage treatment according to claim 1,
wherein, in the step (a), the highest internal liquid temperature, which is a liquid temperature in a portion having the highest liquid temperature within the solution becomes lower than or equal to a temperature which is 7° C. lower than a melting point of a solvent in an unfrozen state.

14. The cell structure for brain damage treatment according to claim 1,
wherein the cell structure is a cell structure obtained by mixing the biocompatible macromolecular blocks and the cells and culturing the mixture for 10 hours or longer.

15. A cell structure for brain damage treatment which is obtained by merging a plurality of the cell structures for brain damage treatment according to claim 1.

16. A method for producing the cell structure for brain damage treatment according to claim 1, the method comprising:
a step of mixing cells and biocompatible macromolecular blocks of which the tap density is 10 mg/cm$^3$ to 500 mg/cm³ or a value obtained by dividing a square root of a cross-sectional area in a two-dimensional cross-sectional image by a peripheral length is 0.01 to 0.13, and culturing the mixture for 10 hours or longer.

17. A brain damage treatment agent comprising:
the cell structure for brain damage treatment according to claim 1.

18. A method for treating brain damage, the method comprising: a step of administering a cell structure for brain damage treatment to a patient with brain damage,
wherein the cell structure for brain damage treatment contains biocompatible macromolecular blocks and at least one kind of cell and a plurality of the biocompatible macromolecular blocks are disposed in gaps between a plurality of at least one kind of cell,
wherein the tap density of the biocompatible macromolecular block is 10 mg/cm³ to 500 mg/cm³ or a value obtained by dividing a square root of a cross-sectional area in a two-dimensional cross-sectional image of the biocompatible macromolecular block by a peripheral length is 0.01 to 0.13,
wherein the biocompatible macromolecular block is a biocompatible macromolecular block produced through a method including
a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and
a step (b) of freeze-drying the frozen biocompatible macromolecules which have been obtained in the step (a).

19. The method for treating brain damage according to claim 18,
wherein the cells include at least mesenchymal stem cells and/or bone marrow cells.

20. The method for treating brain damage according to claim 18,
wherein the number of cells, to be administered, per administration is $1.0 \times 10^5$ to $1.0 \times 10^7$ pieces/kg body weight.

21. The method for treating brain damage according to claim 18,
wherein the brain damage includes brain injury, hypoxic-ischemic brain damage, cerebral infarction, and/or cerebral stroke.

22. The method for treating brain damage according to claim 18,
wherein the size of one of the biocompatible macromolecular blocks is 10 µm to 300 µm.

23. The method for treating brain damage according to claim 18,
wherein the thickness or the diameter of the cell structure is 400 µm to 3 cm.

24. The method for treating brain damage according to claim 18,
wherein the cell structure includes 0.0000001 µg to 1 µg of a biocompatible macromolecular block per cell.

25. The method for treating brain damage according to claim 18,
wherein the biocompatible macromolecular block consists of a recombinant peptide.

26. The method for treating brain damage according to claim 25,
wherein the recombinant peptide is any of
a peptide formed of an amino acid sequence described in SEQ ID No: 1,
a peptide formed of an amino acid sequence in which one or a plurality of amino acids are deleted, substituted, or added in the amino acid sequence described in SEQ ID No: 1, and has biocompatibility, or
a peptide formed of an amino acid sequence having 80% or more sequence identity to the amino acid sequence described in SEQ ID No: 1, and has biocompatibility.

27. The method for treating brain damage according to claim 18,
wherein, in the biocompatible macromolecular block, the biocompatible macromolecules are cross-linked using heat, ultraviolet rays, or enzymes.

28. The method for treating brain damage according to claim 18,
wherein the biocompatible macromolecular block is in a granule form obtained by grinding a porous body of a biocompatible macromolecule.

29. The method for treating brain damage according to claim 18,
wherein the method of producing further comprises a step (c) of grinding a porous body which has been obtained in the step (b).

30. The method for treating brain damage according to claim 18,
wherein, in the step (a), the highest internal liquid temperature, which is a liquid temperature in a portion having the highest liquid temperature within the solution becomes lower than or equal to a temperature which is 7° C. lower than a melting point of a solvent in an unfrozen state.

31. The method for treating brain damage according to claim 18,
wherein the cell structure is a cell structure obtained by mixing the biocompatible macromolecular blocks and the cells and culturing the mixture for 10 hours or longer.

32. The method for treating brain damage according to claim 18, wherein the cell structure for brain damage treatment is obtained by merging a plurality of the cell structures for brain damage treatment.

33. The method for treating brain damage according to claim 18, wherein the biocompatible macromolecular blocks are blocks of heat-crosslinked polypeptide.

* * * * *